(12) United States Patent
Toone et al.

(10) Patent No.: US 7,598,092 B2
(45) Date of Patent: Oct. 6, 2009

(54) METHODS, DEVICES, SYSTEMS AND COMPUTER PROGRAM PRODUCTS FOR STOCHASTIC, COMPETITIVE, FORCE-BASED ANALYTE DETECTION

(76) Inventors: Eric Toone, 2601 Evans St., Durham, NC (US) 27705; Piotr Marszalek, 102 Shadow Ridge Pl., Chapel Hill, NC (US) 27516; Robert L. Clark, 104 Commons Way, Chapel Hill, NC (US) 27516; Phil Snyder, 4617 American Dr., Durham, NC (US) 27705

( * ) Notice: Subject to any disclaimer, the term of this patent is extended or adjusted under 35 U.S.C. 154(b) by 0 days.

(21) Appl. No.: 11/759,468

(22) Filed: Jun. 7, 2007

(65) Prior Publication Data
US 2008/0090259 A1 Apr. 17, 2008

Related U.S. Application Data

(60) Provisional application No. 60/804,213, filed on Jun. 8, 2006.

(51) Int. Cl.
*G01N 33/543* (2006.01)
(52) U.S. Cl. .................. 436/518; 435/287.1; 435/287.2; 436/524; 436/525
(58) Field of Classification Search .................. None
See application file for complete search history.

(56) References Cited

U.S. PATENT DOCUMENTS

| | | | |
|---|---|---|---|
| 5,363,697 A | 11/1994 | Nakagawa | |
| 5,372,930 A | 12/1994 | Colton et al. | |
| 6,167,748 B1 * | 1/2001 | Britton et al. | 73/24.06 |
| 6,763,705 B1 * | 7/2004 | Thundat et al. | 73/64.53 |
| 6,798,226 B2 * | 9/2004 | Altmann et al. | 324/754 |
| 6,987,898 B2 | 1/2006 | Tran et al. | |
| 7,105,358 B2 * | 9/2006 | Majumdar et al. | 436/518 |

OTHER PUBLICATIONS

International Search Report and Written Opinion (10 pages), Corresponding to International Application PCT/US07/13439, Mailing Date: Sep. 16, 2008.
Burg et al. "Weighing of biomolecules, single cells and single nanoparticles in fluid" *Nature* 446:1066-1069 (2007).
Gupta at al. "Anomalous resonance in a nanomechanical biosensor" *PNAS* 703(36):133362-133367 (2006).
"Cantilevers measure solution-phase thermodynamics" *Analytical Chemistry* 3232 (2007).

* cited by examiner

*Primary Examiner*—Christopher L Chin
(74) *Attorney, Agent, or Firm*—Myers Bigel Sibley & Sajovec

(57) ABSTRACT

A cantilever array can be positioned adjacent a surface in the presence of a sample. The cantilever array includes a plurality of cantilevers having one member of a specific binding pair thereon. The surface includes the other member of a specific binding pair. Binding between the members of the binding pair on the cantilevers and the surface can be detected. The presence, absence and/or concentration of a member of the specific binding pair in the sample can be detected based on the detected binding between the specific binding pair member on the cantilevers and the specific binding pair member on the surface.

19 Claims, 13 Drawing Sheets

STEP 1: INSERT CARTRIDGES AND SAMPLE ( MICROCANTILEVERS FORCED INTO SUBSTRATE TIPS )
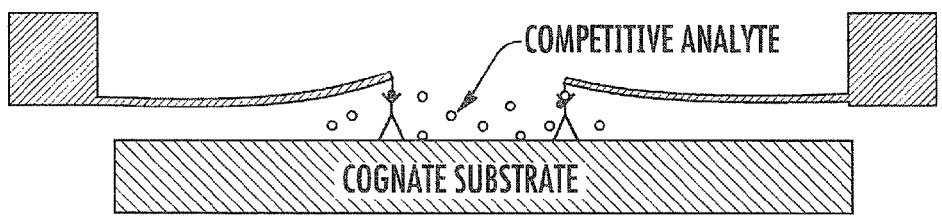
STEP 2: USE ACTUATOR TO SEPARATE CARTRIDGES AT A FIXED RATE ( FIXED BY DESIGN )
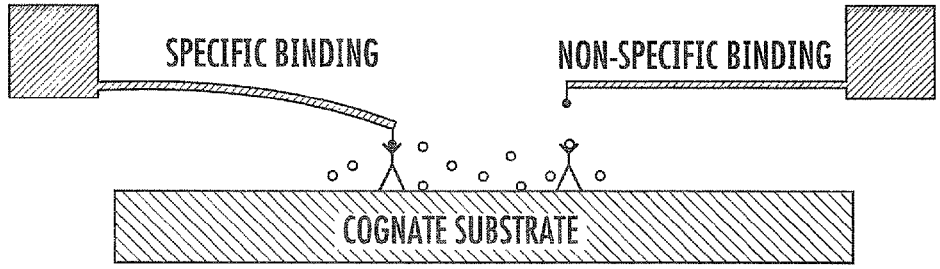
STEP 3: QUANTIFY MAGNITUDE OF OSCILLATION AT RUPTURE.
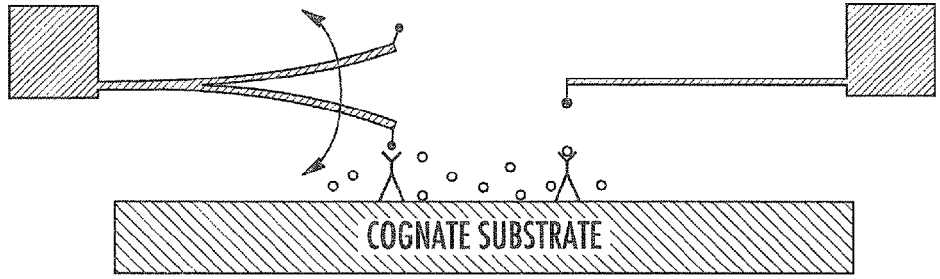
FIG. 10

METHODS, DEVICES, SYSTEMS AND COMPUTER PROGRAM PRODUCTS FOR STOCHASTIC, COMPETITIVE, FORCE-BASED ANALYTE DETECTION

RELATED APPLICATIONS

This application claims priority to U.S. Provisional Application Ser. No. 60/804,213, filed Jun. 8, 2006, the disclosure of which is incorporated herein by reference in its entirety.

FIELD OF THE INVENTION

The present invention is directed to methods and devices for stochastic, competitive force-based analyte detection.

BACKGROUND

Contemporary diagnostic medicine increasingly utilizes the quantitative measurement of biochemical markers. Many techniques for detecting protein and small molecule analytes clinically utilize antibody-based diagnostics. In general, immunodiagnostics are divided into two broad groups: 1) quantitative assays—prototypically ELISA and its variants—that require significant time (hours), expertise and equipment (spectrophotometer). These assays are typically performed in hospital clinical laboratories; and 2) qualitative assays—prototypically particulate labeled lateral flow immunochromatographic devices—that are rapid (minutes), and require no special expertise or equipment. These assays are suitable for both point-of-care (e.g. rapid strep, influenza) and home use (pregnancy, ovulation) applications, but generally lack the capacity to provide quantitative information.

In many instances, more rapid quantitative analyte information could be used for effective treatment decisions, for example, in cardiovascular medicine. Emergency departments are presented with nearly 8 million people annually with chest pain. The diagnosis of acute cardiovascular syndrome (ACS) can be exceptionally difficult; misdiagnosis rates have been estimated at as high as 12%, with resulting morbidity and mortality and significant associated malpractice costs. The quantitative determination of biochemical markers is already an important component of ACS diagnosis, but the currently available Enzyme-Linked Immunosorbent Assays (ELISA) or ELISA-type assays can delay the availability of information and reduce point-of-care diagnosis.

Although all ACS patients share a common underlying pathophysiology—atherosclerotic plaque rupture with varying levels of superimposed thrombus and/or distal embolization—they can present a remarkable constellation of symptoms. Classic ACS includes deep, generalized or poorly localized pain or discomfort in the chest or arm clearly associated with physical or emotional stress and relieved promptly by sublingual nitroglycerin. (Gibbons, Chatterjee et al. 1999) Many patients show no chest pain, but present with jaw, neck, ear or epigastric discomfort. Atypical presentation include recent onset indigestion, stabbing chest pain, nausea and vomiting, weakness, dizziness, palpitations, cold perspiration and a sense of impending doom.

Current practice evaluates ACS through electrocardiogram (ECG) and physical assessment. The 12-lead ECG is the primary diagnostic standard in the ER evaluation of ACS. (Timmis 1990) ST-segment elevation is the primary anomaly signifying underlying disease, but other deviations, such as ST-segment depression or deep T-wave inversion, identify high-risk patients. (Savonitto, Ardission et al. 1999) Unfortunately, many patients—perhaps as many as 40%—present with normal ECG. A range of alternative risk stratification algorithms have also been investigated; other than the widely used Goldman protocol (Goldman, Cook et al. 1988) and TIMI risk score, (Antman, Cohen et al. 2000). However, many provide a limited short-term prognostic value.

ACS diagnosis can be performed through the evaluation of biochemical markers. (de Winter, Koster et al. 1995) However, the utility of biochemical evaluation of cardiac patients can be substantially diminished by the clinical chemistry now used for diagnosis. Many assays now in use are variants of so-called sandwich immunoassays. (Van Blerk, Maes et al. 1992; Heeschen, Goldmann et al. 1999; Wu 1999; Oh, Foster et al. 2000; Venge, Lindahl et al. 2001) In such assays, a first antibody to an analyte of interest is affixed to a label that can be visualized either directly (metal or latex sol) or indirectly (enzyme). The presence of analyte is detected through the use of a second "capture" antibody, typically immobilized to some surface, forming a "sandwich" of labeled antibody/analyte/capture antibody. Through appropriate calibration, some versions of the assay can be quantified. However, the tests can be slow (hours) and require major instrumentation for read-out, a requirement incompatible with point-of-care use. Both requirements significantly delay the acquisition of important diagnostic information; although recent recommendations call for no more than 1-hour turnaround, this goal is frequently missed. (Wu, Apple et al. 1999; Alpert, Thygesen et al. 2000; Brunwald, Antman et al. 2002) Some attempts have been made to develop laboratory test sites near the ER, but a significant fraction of the delay is fundamental, and related to the nature of the assay. (Lee-Lewandrowski, Corboy et al. 2003) The development of rapid, accurate point-of-care diagnostic devices may have an impact on the diagnosis of ACS and on the resulting morbidity and mortality.

SUMMARY OF THE INVENTION

According to embodiments of the invention, devices, methods and computer program products are provided for detecting the presence, absence and/or concentration of a member of a specific binding pair in a sample using a stochastic, competitive force-based detection of analyte. Although embodiments according to the invention discussed herein using a microcantilever device, any transduction device capable of detecting forces on the order of single specific non-covalent interactions, for example, an antibody binding to a cognate antigen, can be used.

In particular, a cantilever array can be positioned adjacent a surface in the presence of a sample. The cantilever array includes a plurality of cantilevers having one member of a specific binding pair thereon. The surface includes the other member of a specific binding pair. Binding between the members of the binding pair on the cantilevers and the surface can be detected, for example, by the force signature during an approach-retract cycle. The presence, absence and/or concentration of a member of the specific binding pair in the sample can be detected and/or quantitated based on the detected binding between the specific binding pair member on the cantilevers and the specific binding pair member on the surface in the presence of soluble analyte. For example, the concentration of a member of the specific binding pair can be correlated to a diminished likelihood of binding between the specific binding pair member on the cantilevers and the specific binding pair member on the surface.

In some embodiments, the sample is a solution including a member or members of the specific binding pair. If binding occurs between the binding pair member in the solution and a binding pair member on the cantilever and/or on the surface, then fewer binding between the binding pair members on the cantilever and the surface can occur. Stated otherwise, the binding pair member in the sample competes with the binding pair member on the cantilever and/or on the surface. The number of binding can be used to determine the concentration of the binder in the solution, for example, by comparing the measured binding with known quantities of binding for a known concentration of the binder in the solution.

The binding can be detected using various techniques. For example, a force can be applied to separate the cantilever array from the surface. The average force needed to separate the cantilevers from the surface can be detected using optical or piezoelectric techniques. The average rupture force is dependent on the affinity of the binding pair. If the presentation and retraction of the same binding pair occurs in the presence of a sample including a concentration of one of the binders can generally produce a diminished average rupture force, which is dependent on the affinity of the soluble binder for the immobilized binder and on the concentration of the soluble binder. The average rupture force of known concentrations can be used to calibrate a device so that quantitative measurement of binder concentrations in unknown samples can be made.

In some embodiments, methods for determining a concentration of a first member of a specific binding pair in a sample include contacting a sample including the first member of the specific binding pair with a second member of the specific binding pair. A probability of binding is determined using a force signature of a binding event between the first and second members of the specific binding pairs. A concentration of the first member of the specific binding pair is determined based on the probability of binding.

In particular embodiments, determining a probability of binding includes using a force signature from binding on a cantilever array that is in contact with the sample. The cantilever array can include a plurality of cantilevers. Each of the cantilevers can have a first surface including the first member of the specific binding pair and a second surface including the second member of the specific binding pair.

In particular embodiments, determining a probability of binding includes using a force signature from binding using an optical tweezer and/or a magnetic tweezer.

According to further embodiments of the current invention, a device for determining a concentration of a first member of a specific binding pair in a sample includes a sample chamber configured to receive a sample including the first member of the specific binding pair and to contact the first member with a second member of the specific binding pair. A probability evaluation module/controller is configured to determine a probability of binding using a force signature of a binding event between the first and second members of the specific binding pairs. A concentration evaluation module/controller is configured to determine a concentration of the first member of the specific binding pair based on the probability of binding.

In particular embodiments, the concentration evaluation module is configured to determine a probability of binding using a force signature from binding on a cantilever array that is in contact with the sample. The cantilever array includes a plurality of cantilevers. Each of the cantilevers has a first surface including the first member of the specific binding pair and a second surface including the second member of the specific binding pair.

In particular embodiments, the concentration evaluation module is configured to determine a probability of binding using a force signature from binding using an optical tweezer.

DESCRIPTION OF THE DRAWINGS

FIG. 10 is a schematic diagram of sensors and method according to embodiments of the present invention illustrating the steps and the response of two of the microcantilevers in an array.

DESCRIPTION OF EMBODIMENTS OF THE INVENTION

Figure 1:
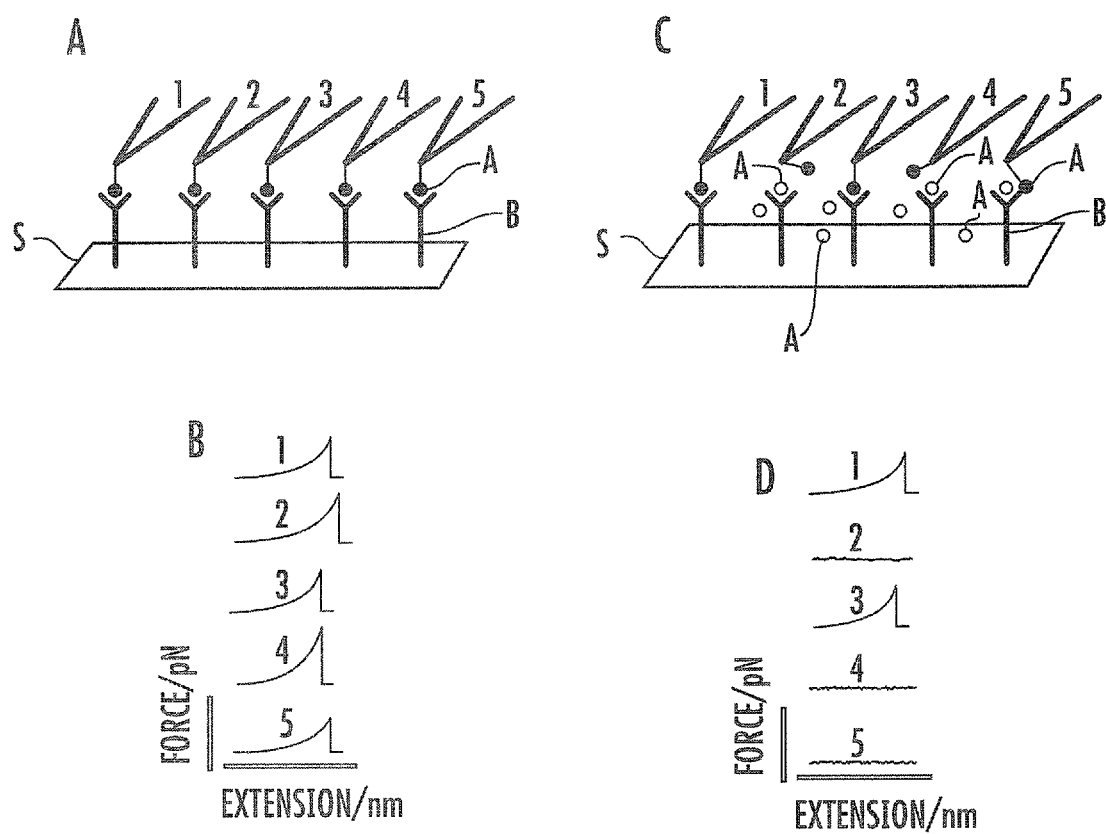
FIG. 1A is a schematic diagram of a plurality cantilevers illustrating binding events between the cantilevers in the absence of a sample.
FIG. 1B is a graph of the force as a function of an extension distance illustrating a rupture force when the microcantilevers of FIG. 1A are separated.
FIG. 1C is a schematic diagram of the plurality cantilevers of FIG. 1A illustrating a reduction in binding events due to competitive binders when the cantilevers are in the presence of a sample that includes one member of the specific binding pair.
FIG. 1D is a graph of the force as a function of an extension distance illustrating a rupture force when the microcantilevers of FIG. 1C are separated.
FIG. 1E is a flow diagram illustrating biochemical markers of ACS. IL: interleukin; MMP: matrix metalloprotease; MPO: myeloperoxidase; ICAM: intracellular adhesion molecule; VCAM: vascular adhesion molecule; PIGF: placental growth factor; PAPP-A: pregnancy-associated plasma protein A; CRP: C-reactive protein; IMA: ischemia-modified albumin; FFAu: unbound free fatty acids; Tn: troponins; NT-BNP: N-terminal B-type natriuretic peptide.
Figure 1E:
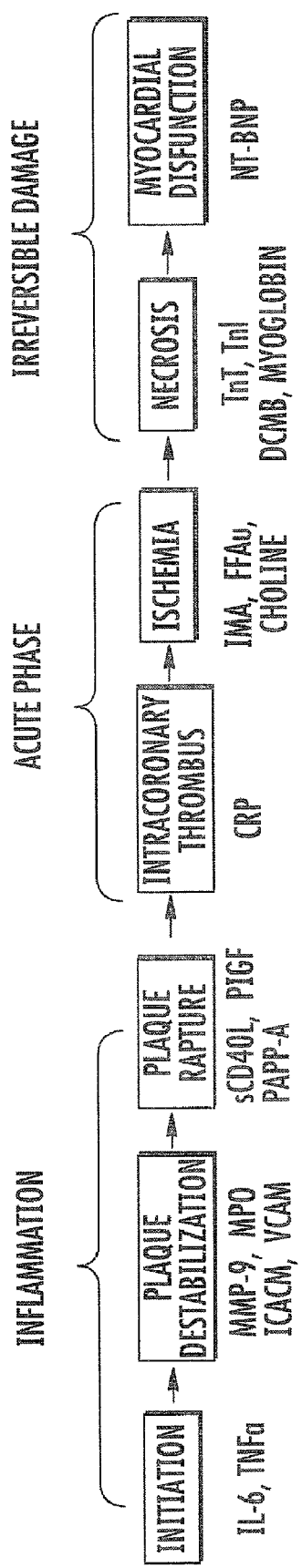

The present invention now can be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure can be thorough and complete, and can fully convey the scope of the invention to those skilled in the art.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

"Target molecule" as used herein refers to any type of molecule for which detection (including quantitative detection) may be desired, including but not limited to peptides, proteins, nucleic acids, sugars, mono- and polysaccharides, lipids, lipoproteins, whole cells, etc.

"Binding pair" refers to a pair of molecules, one of which may be a target molecule or probe, which members of said pair of molecules specifically and selectively bind to one another. Examples of suitable binding pairs include, but are not limited to: nucleic acid and nucleic acid; protein or peptide and nucleic acid; protein or peptide and protein or peptide; antigens and antibodies; receptors and ligands, haptens, or polysaccharides, complementary nucleic acids, pharmaceutical compounds, etc. Members of binding pairs are sometimes also referred to as "binders" herein.

The term "nucleic acid" as used herein refers to any nucleic acid, including both DNA and RNA. Nucleic acids of the present invention are typically polynucleic acids; that is, polymers of individual nucleotides that are covalently joined by 3', 5' phosphodiester bonds.

The term "complementary nucleic acid" as used herein refers to any nucleic acid, including oligonucleotide probes, that specifically binds to another nucleic acid to form a hybridized nucleic acid.

The term "probe" as used herein refers to a molecule which specifically binds to another molecule in a binding pair, which probe molecule may be used to determine the presence or absence of the other molecule. Probes may be any member of a binding pair and include, for example, proteins, peptides, natural or synthetic nucleic acids such as DNA or RNA, etc.

While the methods and apparatus of the present invention are sometimes explained with respect to analyte and receptor binding pairs herein for purposes of clarity, it is to be understood that the methods and apparatus of the instant invention may be applied to other targets, probes, and other binders.

As shown in FIGS. 1A and 1C, a plurality of cantilevers 1, 2, 3, 4, 5 include at least one member A of a specific binding pair. The other member B of the specific binding pair is positioned on a surface S. In FIG. 1A, the cantilevers 1, 2, 3, 4, 5 are placed in contact with the members B on the surface, and a binding event occurs. The binding events can be detected, for example, by subsequently separating the cantilevers 1, 2, 3, 4, 5 from the surface and plotting the separation force as a function of extension distance as shown in FIG. 1B.

In contrast, as shown in FIG. 1C, when the cantilevers 1, 2, 3, 4, 5 (including the member A of the specific binding pair) are placed in a solution that includes some concentration of the member A, fewer binding events will generally occur. As shown in FIG. 1C, binding events occur between some of the members B of the binding pair and some of the members A from the solution. As shown in FIG. 1C, binding events only occur between cantilevers 1 and 3 because the members B that correspond to cantilevers 2, 4, and 5 have experienced binding with binding pair members A from the solution. A graph of the separation force as a function of extension distance is shown in FIG. 1D and illustrates that binding events are detected at cantilevers 1 and 3.

Without wishing to be bound by theory, if the concentration of the binding pair member A in the solution of FIG. 1C is increased, it is expected that more binding events would occur between the binding pair members B and the binding pair members A in the solution. Consequently, fewer binding events would occur between the binding pair members A on the cantilevers 1, 2, 3, 4, 5 and the members B on the surface. In other words, as the concentration of the binding pair member A in the solution is increased, the number of binding events detected by the cantilevers 1, 2, 3, 4, 5 decreases. In some embodiments, an unknown concentration of a binder can be determined by comparing the detected binding events to experimentally determined binding events for a known sample concentration of the binder/analyte.

The cantilevers 1, 2, 3, 4, 5 are illustrated as having a single binding pair member A thereon; however, the cantilevers 1, 2, 3, 4, 5 can each include more than one binding pair member A.

Although FIGS. 1A-1D are illustrated with respect to cantilevers 1, 2, 3, 4, 5, any number of cantilevers may be used, including arrays with several hundred or more cantilevers. In some embodiments, binding events can be detected by one or more cantilever by repeatedly placing the cantilever (with a binder thereon) in contact with another binder on a surface. In particular embodiments, a single cantilever can be used to repeatedly detect binding events and to determine a probability of binding, which can then be correlated to a concentration of analyte in a solution.

Although embodiments according to the current invention are described herein with respect to microcantilever arrays, it should be understood that other techniques can be used to detect binding events, including techniques that stochastically evaluate the binary probability of binding events, for example, using a force signature of binding and relating that probability to the concentration of soluble analyte in a solution. Example of such techniques include optical tweezers and magnetic tweezers. For example, optical tweezers using optical gradient forces from a beam of light can manipulate the position of a small dielectric particle immersed in a fluid medium whose refractive index is smaller than that of the particle. Optical tweezer techniques may be used to enable manipulation of reflecting, absorbing and low dielectric constant particles as well. A single particle can be manipulated by using a single beam of light to generate a single optical trap, or multiple particles using multiple beams of light may be employed to determine a force signature of binding. The force signature of binding can then be correlated to determine a concentration of soluble analyte in a solution, for example, using a reference database of known concentrations and corresponding force signatures as described herein. For example, optical tweezers can be used instead of the cantilevers 1, 2, 3, 4, 5 in FIGS. 1A-1D.

When a microcantilever bearing a member of a binding pair is brought into contact with or adjacent a surface bearing the other member of the binding pair, a binding interaction can occur. Binding events can be determined based on a determination of bending or deflection of the cantilever, for example, using optical or electrical methods. Optical methods of detecting binding events include projecting a light source to the cantilever surface at an angle and detecting the reflected beam. If the cantilever is deflected during an approach/retract cycle due to a binding event, the light is reflected at a different angle than the light would be reflected if a binding event had not occurred. Electrical methods to detect a binding event can use piezoresistors. Piezoresistive materials, such as doped silicon, can be integrated into the cantilevers. For example, the cantilevers can be formed of silicon, and a dopant may be implanted into the silicon at the cantilever's base. Any suitable piezoresistive materials can be used. When the piezoresistive material is strained, the resistance of the material changes. If a binding event occurs, the cantilever's bending may initiate strain in the piezoresistor, which results in a change in its electrical conductivity. The conductance can be monitored, for example, using known techniques.

According to embodiments of the present invention, microcantilevers having one member of a binding pair thereon are brought into contact with respective surfaces bearing the other member of the binding pair in the presence of a solution that includes an unknown concentration of one of the binding pairs. Binding events may be detected. For example, a force may be applied to the microcantilevers, which may be sufficient to rupture the binding interaction. Various force signatures can be determined for the binding interaction, including an average rupture force (related to the likelihood of binding) and/or a probability of rupture for a given force (related to the stability of the bound complex). For example, a force spectrogram can be used to relate the average rupture force to the likelihood of binding. The probability of rupture for a given force may be obtained by applying a force to the microcantilevers and measuring how many microcantilevers report rupture as a result.

The force signature of the binding interaction, such as the average rupture force and/or the probability of rupture, can be correlated to the concentration of the analyte (binder) in the solution. The average rupture force and/or probability of rupture may be compared to the average rupture force or probability of rupture corresponding to various known concentrations of samples containing the member of the binding pair. The concentration of binders in the solution may be estimated based on the comparison to average rupture forces and/or rupture probabilities obtained from known concentrations.

In some embodiments, an array of microcantilvers configured to detect members of one, two or more different binding pairs may be present on a biosensing substrate. The respective surfaces of the microcantilevers may be brought together in the presence of a solution having an unknown concentration of one or more of the members of the binding pairs and a separation force may be applied as described above. The probability of rupture and/or the average rupture force for each of the different binding pairs may be compared to values for known concentrations of the binding pair members. Accordingly, the concentrations of more than one binder in a solution may be estimated using a single device.

In some embodiments, the probability of rupture and/or the average rupture force for known concentrations of binders in solution may be determined experimentally. For example, microcantilevers having one member of a binding pair thereon can be brought into contact with respective surfaces bearing the other member of the binding pair in the presence of various solutions that include a known concentration of one of the binding pairs. An average rupture force and/or a probability of rupture for a given force can be obtained for different known solution concentrations. Without wishing to be bound by theory, it is noted that higher concentrations may produce a diminished rupture force due to competitive binding to the soluble binder in the solution. The probability of rupture and/or average rupture force for known concentrations can be stored, for example, in a database or table.

In particular embodiments, a blood sample may be evaluated for more than one biomarker, for example, related to acute cardiovascular syndrome (ACS). For example, microcantilever array can be configured to detect concentrations of biomarkers related to ACS, such as myoglobin, creatine kinase myocardial band (CK-MB), the cardiac troponins (TnT, TnI), myeloperoxidase, matrix metalloprotease 9, pregnancy-associated plasma protein and placental growth factor. Although embodiments of the invention are described herein with respect to markers related to ACS, it should be understood that other biological and non-biological markers may be detected, including in clinical or environmental samples. Examples of samples that may be used include the following: blood, urine, and water. Opaque, translucent or transparent samples can be used. Examples of analytes that may be quantitatively evaluated include biomedical analytes, including makers of cardiovascular disease, including myocardial infarct (myoglobic, troponins, myloperoxidase, matrix metalloproteinase 9, etc), primary (catecholamines, eg epinephrine, norepinepherine, vanillylmandelic acid) and secondary (cortical, liver enzymes) hypertension therapeutic and abusive drug levels, creatinine, billirubin, various cancer antigens (prostate specific antigen), liver enzymes (alanine aminotransferase, aspartate aminotransferase), and environmental analytes, including organic and inorganic compounds and wastes.

Embodiments of the present invention include computer program products and/or hardware configured to implement cantilever biosensing techniques discussed herein.

EXAMPLES

I. Biochemical Markers and the Diagnosis of Acute Cardiac Syndrome (ACS)

The onset of ACS produces a range of biochemical consequences, reflecting natural efforts at damage repair and, ultimately, markers of cellular death. These markers are universal, and biochemical markers of myocardial necrosis are a test for ACS. The most commonly used markers are myoglobin, creatine kinase myocardial band (CK-MB) and the cardiac troponins (TnT, TnI). All three markers appear at varying times following myocardial infarct. Myoglobin elevation is generally observable the earliest of any marker, at 1 to 2 hours after onset of necrosis. Because of the high rate of false positives, especially in qualitative tests such as the widely used electrophoretic techniques, an assay for myoglobin is generally used only for initial marker sampling. (Kontos, Anderson et al. 1999) CK-MB has been used for decades as a biochemical marker of AMI, although it too provides some level of false positive results. Newer qualitative tests for CK-MB, as opposed to qualitative electrophoretic tests, offer significantly improved prognostication capability. A recent study of over 2000 patients admitted with chest pain but lacking ST-segment elevation showed the remarkable accuracy of either elevated 0- or 3-hour CK-MB levels or a doubling of CK-MB concentrations over that time period. (Kontos, Anderson et al. 1999) One biochemical marker with a predictive index is unquestionably troponin, and this species can be used as a marker for myocardial necrosis. (Polanczyk, Lee et al. 1998; Wu, Apple et al. 1999; Alpert, Thygesen et al. 2000) Biochemical evaluation of patients arriving in the emergency department allows early diagnosis of patients with even minor levels of necrosis.

Early markers, such as myeloperoxidase, matrix metalloprotease 9, pregnancy-associated plasma protein and placental growth factor could also be of value in early detection of incipient ACS. (Kai, Ikeda et al. 1998; Zhang, Brennan et al. 2001; Buffon, Biasucci et al. 2002; Blankenberg, Rupprecht et al. 2003; Heeschen, Fichtlscherer et al. 2003; Lund, Qin et al. 2003; Heeschen, Dimmeler et al. 2004)

II. Exemplary Sensor Device

Figure 2:
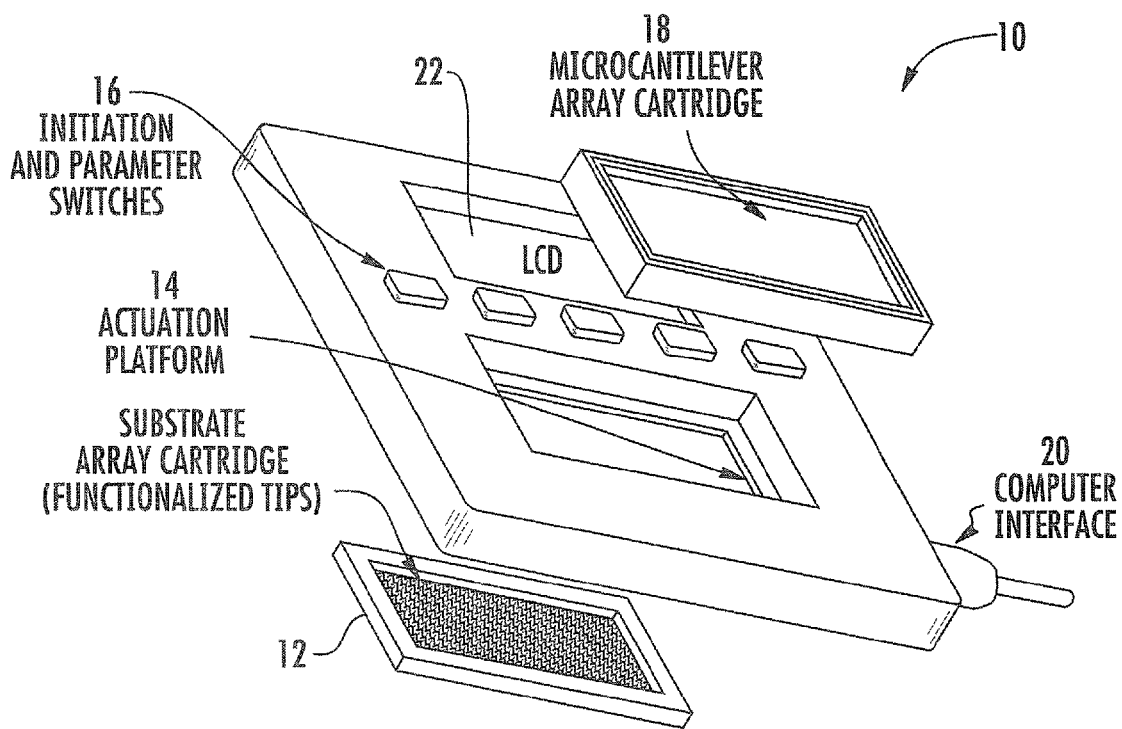
FIG. 2 is a schematic diagram of a cantilever sensor design platform according to embodiments of the present invention.

Microcantilever arrays have been integrated on a stand-alone chip (7×10 mm) to realize an atomic force microscope with individual actuation, detection, and control of each microcantilever (Hafizovic, Barrettino et al. 2004). FIG. 2 is an exemplary sensor system. The sensory system can include a basic instrument, which can be the size of a hand-held calculator and incorporates the necessary power and signal conditioning electronics required for operation of the sensing system. Microcantilever arrays can be inserted into the basic instrument. For example, as illustrated in FIG. 2, a sensing device 10 can include a removable substrate array cartridge 12 that is connectable to an actuation platform 14. A microcantilever array cartridge 18 can also be removably inserted in the device 10. The device further includes controls or initiation and parameter switches 16, a display 22 and a computer interface 20. The substrate array cartridge 12 can be manufactured with "tips" on the surface functionalized as necessary for the diagnostic test desired. In conventional atomic force microscopy, the tips are typically placed on the microcantilever; however, to facilitate the manufacturing process for threshold sensing, locating the tips on the surface of the substrate 12 reduces complexity of design and manufacturing. The tips can have a radius of about 50 nm or other suitable dimensions, such as dimensions typical of AFM microcantilevers. The substrate 12 and/or the microcantilever array cartridge 18 can be a disposable component of the diagnostic device 10 and can be snapped into place, e.g., from the under or upper side of the hand-held diagnostic system as illustrated in FIG. 2, and once in place, the desired sample (blood, serum, urine, etc.) can be applied to the surface in the form of a drop with a simple syringe.

An array of "diving-board" microcantilevers can be fabricated such that they can be "snapped" into place from the top surface of the device 10 and effectively seal the now enclosed sample. Each microcantilever can be immobilized at the end over a surface area of approximately 50 μm×50 μm with one half of the binding pair; the other half of the binding pair can be immobilized on the tip of the substrate cartridge 12.

Assuming that an array of approximately 500 microcantilevers is sufficient to provide statistically significant results, the dimension of the cartridges need only be on the order of about 1 cm×1 cm. When snapped into place, the tolerance on the assembly can be maintained such that all microcantilevers engage the substrate 12, which is configured with functionalized tips. Some microcantilevers may be deflected on the order of nanometers during the assembly process and some may deflected on the order of micrometers; however, design specifications can be provided such that all microcantilevers undergo a nominal deflection during contact. The inconsistency in deflection is "by design" and can ensure that substantially all microcantilevers engage functionalized tips; however, it removes barriers to implementation associated with variations in tolerance for typical manufacturing processes. Furthermore, since the sensor array can be used to simply categorize the force associated with unbinding as either "an event" or a "non event," it matters not the order in which microcantilevers separate from the substrate.

Since loading rate is a parameter in molecular force measurements (Evans and Ritchie 1997), the instrument can be designed such that the two cartridges 12, 18 are separated at a fixed rate by the simple flip of a switch that engages an actuator. The dynamic response associated with the separation of the microcantilever from the surface can be quantified by monitoring the displacement response of the microcantilever either through optical, piezoelectric, or piezoresistive sensing methods. The magnitude of the dynamic response response is related to the impulse response of the structure and the corresponding deflection (due to force) at rupture. Signal processing can be used to effectively quantify the separation as an event associated with non-specific binding (weak forces—small dynamic response) or specific binding (strong forces—large dynamic response). In so doing, binary results can be obtained, and the results of these binary decisions can be placed in bins and counted. With an array of microcantilevers, one can obtain a statistical measure through single molecule threshold sensing.

The substrate array cartridge 12 and the microcantilever array cartridge 18 illustrated in FIG. 2 can be disposable units (~1 cm×1 cm) and can be configured for different binding events—and thus different applications. The hand-held diagnostic device can allow the user to select the particular assay and thus modify actuation rate as necessary. A computer interface can also afford opportunities to upgrade the software as diagnostic assays become available. Basic design principles for loading rates and associated calibrated force measurements to define thresholds for dynamic response measures can be experimentally determined. Sensor system design parameters include optimization of microcantilever design to maximized dynamic response and signal to noise ratio, immobilization chemistry, and binding pair design for myriad biomedical, environmental, food safety and defense applications.

III. Experiments

An experiment for threshold force sensing using an AFM spectrometer operating in single axis force mode has been performed. Murine galectin 3, a lectin specific for the disaccharide lactose, was used as a model receptor and immobilized lactose was used as the ligand. The behavior of the device in the presence of competing soluble lactose demonstrates the sensitivity required for the application proposed. The synthesis of the molecules, the preparation of surfaces and tips, and the results of competitive binding experiments are described below.

A. Synthesis of Molecules

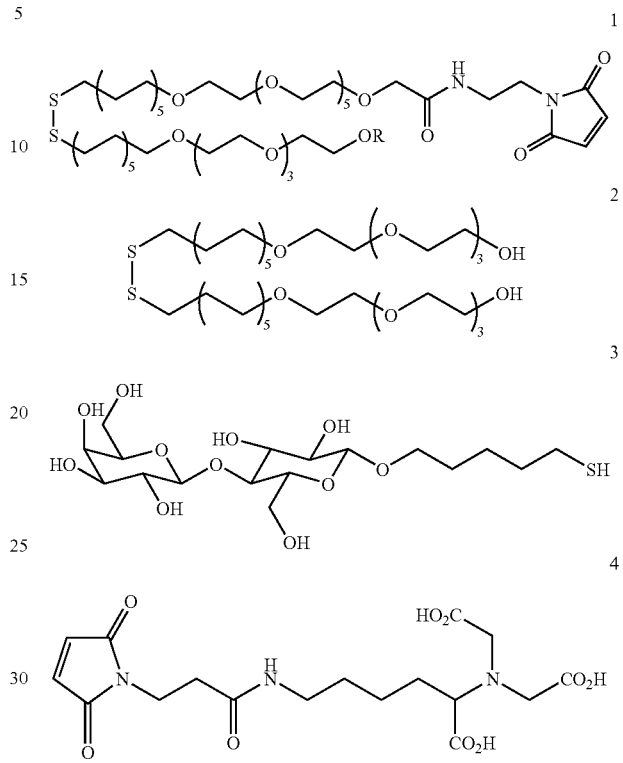

Scheme 1

Immobilized receptor (galectin 3) and ligand (lactose) were prepared as self-assembled monolayers on gold coated surfaces and tips. To minimize non-specific binding, both interactive species were immobilized in a background of oligoethylene glycol. Alkyl disulfides bearing either cross-reactive maleimide-linked oligoethylene glycol 1 (maleimido disulfide) or underivatized oligoethylene glycol 2 (blank disulfide) were synthesized after the methods of Houseman et al. (Houseman, Gawalt et al. 2003). Disulfides were prepared from the parent 1-undecen-11-yl oligo(ethylene glycols) (Palegrosdemange, Simon et al. 1991). The primary alcohol was protected as the methoxymethyl acetal and subjected to photoinduced radical addition of thiolacetic acid as described by Roberts et al., (Roberts, Chen et al. 1998). The thiol was liberated in basic methanol and converted to the 2-pyridyldisulfide with Aldrithiol to provide disulfide donor. Mercaptoundecanyl hexa(ethylene glycol)acetic acid was prepared via alkylation of monoprotected 2, followed by addition of thiolacetic acid to the alkene. Cleavage of the t-butyl ester with trifluoroacetic acid and subsequent basic methanolysis of the thioacetate provided the required monoacid. The acid disulfide was prepared by base-catalyzed disulfide exchange. Following chromatography, the acid was converted to the unsymmetric anhydride and crossed with 2-aminoethyl maleimide in base to provide protected disulfide (Corrie 1994; Antczak, Bauvois et al. 2001). Deprotection in acidic methanol provided 1 in good yield.

Acetobromolactose was prepared as previously described and coupled to 4-penten-1-ol, and subjected to radical addition of thiol acetic acid (Kartha and Jennings 1990; Rodriguez and Stick 1990). Global deprotection in basic methanol provided the desired mercaptopentyl glycoside 3.

Dialkyl disulfides bearing either cross-reactive maleimide-linked oligoethylene glycol 1 (maleimido disulfide) or underivatized oligoethylene glycol 2 (blank disulfide) were synthesized following the general approach of Houseman et al. (Houseman 2003) Mercaptopentyl lactoside 3 was synthesized from acetobromolactose by glycosylation of pent-5-en-1-ol (Kartha & Jennings 1990; Rodriguez & Stick 1990). The resulting pentenyl glycoside was subjected to radical addition of thiol acetic acid; global deprotection in basic methanol provided the desired lactose derivative (Roberts & Chen 1998).

B. Protein Purification

The gene for galectin-3 was obtained by PCR amplification from the plasmid prCBP35s (obtained from Dr. J. L. Wang) and digested with EcoRI and BamHI. The digested PCR product was ligated into a similarly prepared pET28b plasmid and transformed into XL10-Gold Cells. Resultant colonies were isolated, analyzed for insert by PCR, and sequenced to validate coding frame. The validated plasmid was transformed into BL21(DE3) cells via heat shock. Single colonies from this transformation were grown to an $OD_{600}$=0.6-0.8, induced for 4 hours at 37° C. with 125 mg $L^{-1}$ isopropyl thiogalactopyranoside and harvested by centrifugation. The construct yields roughly 20 mg protein per liter of cell growth. Protein was purified in the standard fashion over nickel affinity resin (Novagen).

C. Preparation of Surfaces and Tips.

Model NP silicon nitride, triangular cantelivers (Veeco) were coated sequentially with a 70 Å chromium adhesion layer followed by 230 Å gold layer using an electron-beam metal evaporator (CHA Industries). Formation of self-assembled monolayers (SAMs) on gold using disulfide mixtures has been described previously (Houseman, Gawalt et al. 2003). Briefly, a disulfide mixture with a 0.10 mole fraction of maleimido disulfide in blank disulfide was dissolved in ethanol. Gold-coated cantilevers were submerged in this solution for 12 hours at room temperature and rinsed with ethanol. The cantilevers were submerged for 4 hours at 37° C. in an aqueous solution containing 2.25 mM mercaptopentyl glycoside 3. The ligand-derivatized cantilevers were rinsed with water and ethanol and dried under a stream of $N_2$.

The method of Vogel and coworkers was used to immobilize hexahistidine-tagged proteins to quartz surfaces bearing the metal chelate nitrilotriacetic acid (Schmid, Keller et al. 1997). Briefly, quartz coverslips were oxidized in a boiling solution of peroxide and hydrochloric acid, rinsed thoroughly and dried at 150° C. The surface was silanized with mercaptopropyl trimethoxysilane under vacuum at room temperature for 24 hours. The resulting free thiols were cross-reacted with $N^\alpha$-bis-carboxymethyl-$N^\epsilon$-3-maleimidopropionyl lysine (Schmid, Keller et al. 1997) in 10 mM sodium carbonate buffer (pH=7.00) and charged with 50 mM nickel(II) chloride during 5 minute immersion. After rinsing, the slide was incubated with a solution of hexahistidine-tagged galectin 3 (~50 µM) in 50 mM sodium phosphate (pH 7.50) at 4° C. for one hour. The protein-bearing slide was rinsed with 5 mM imidazole buffer (Tris, pH=7.90) and adhered to a metal disc.

D. Competition Experiments.

Metal discs with adherent protein slides were placed on the magnetic holder of a one-dimensional piezoelectric actuator. Cantilevers were fixed in the liquid chamber of a commercially available atomic force microscope head (Veeco/Digital Instruments) and positioned above the slide. The spring constant of each AFM cantilever was calibrated in solution using the thermal noise method as previously described (Florin 1995). The liquid chamber was filled with buffer containing the appropriate concentration of β-methyl lactose (0-100 mM) and the cell allowed to reach thermal equilibrium. Force measurements were obtained during a retract/approach cycle by manually bringing the surface in close proximity to or in gentle (<200 pN) contact with the tip and then retracting at a rate of 0.205 nm $ms^{-1}$. Gentle contact was essential to minimize nonspecific interaction between the AFM tip and substrate. At each position, a small voltage ramp was used to drive the sample closer to the tip. This process was stopped after the retracting trace revealed an adhesion force, and little indentation was made on approach. The photodiode signal was filtered during acquisition at 500 Hz. Force curves were collected and analyzed in LabView™ software. Although not every approach resulted in interaction between the surface and tip, all forces (exceeding the 15 pN noise background) in the range of 0-200 pN at extensions of 0-200 nm were recorded. The typical experiment constituted 800-1000 individual pulls, resulting in 350-800 measured forces.

The cantilever-based device used in this example used stable, specific immobilization of both receptor and ligand to opposing surfaces. In particular, self-assembled monolayers of alkyldisulfides on gold coated cantilevers were used. The disulfides include a mixture of undecanyl-oligoethylene glycol and maleimide-terminated undecanyl-oligoethylene glycol at a predetermined mole fraction of maleimide (Houseman, Gawalt et al. 2003). The embedded maleimide serves as an anchor point for the attachment of mercaptopentyl lactoside, the immobilized ligand for galectin 3. For the opposing surface, quartz slides functionalized with the metal chelate nitrilotriacetic acid, were used and provided the oriented surface immobilization of hexahistidine-tagged galectin 3 (Schmid, Keller et al. 1997).

Force spectrograms were examined for the dissociation of immobilized lactose and galectin employing nickel(II) coordination complexes. During the AFM experiment, a microcantilever bearing bound lactose contacts a surface bearing galectin 3, resulting in a binding event. Retraction of the cantilever from the surface requires the application of sufficient force to rupture the binding interaction. The repetitive application of this cycle yields force spectrograms with an average rupture force related to the likelihood of binding, a probability in turn related to the stability of the bound complex and the activity of the congnate partners, assuming the experimental design presents no insurmountable kinetic barriers to binding. In the presence of lactose, the average rupture force is diminished, since the probability of protein-surface ligand complexation is diminished by competitive binding.

Figure 3:
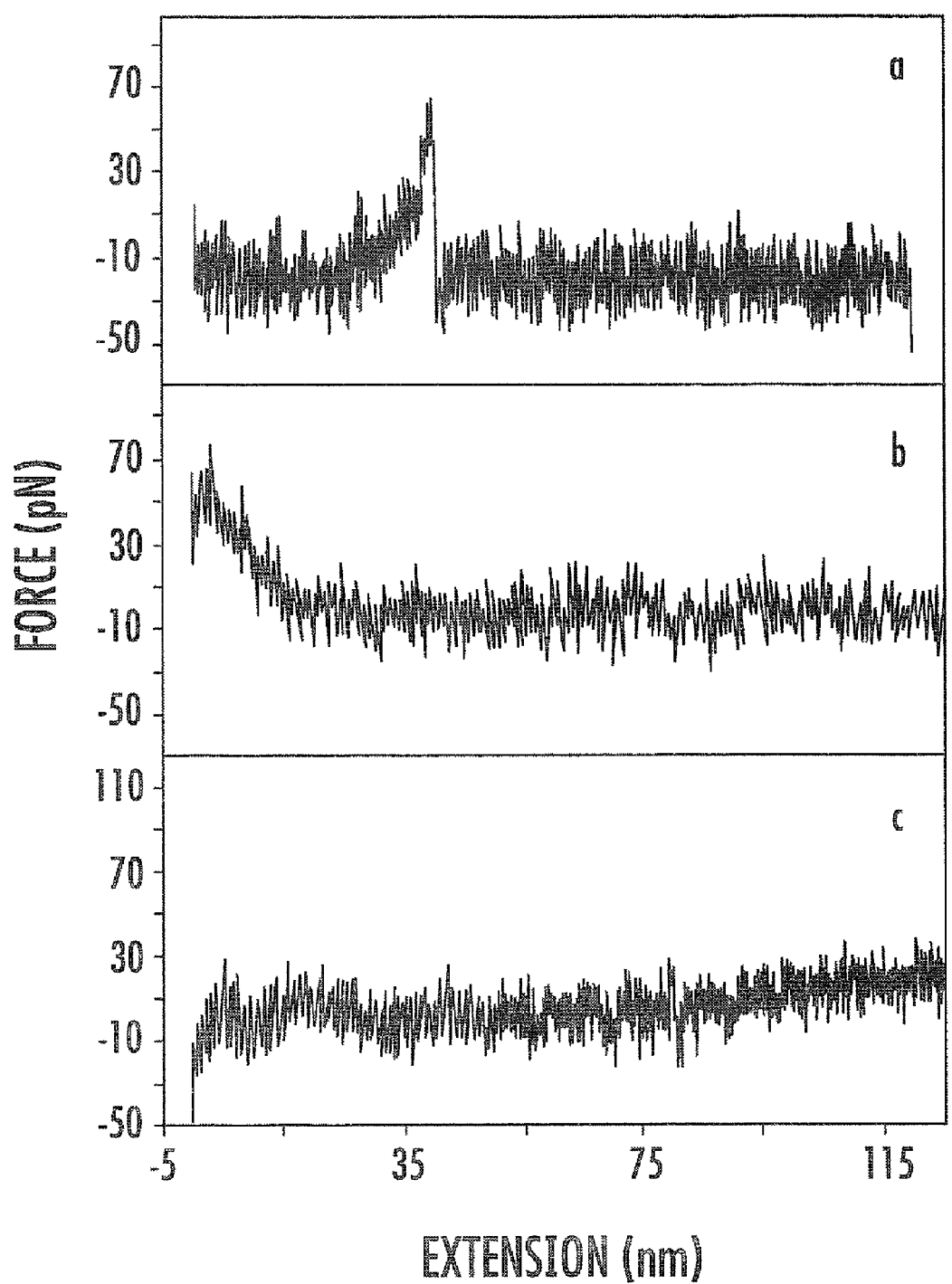
FIG. 3a-3c are graphs of typical force signatures, including force spectrograms obtained with the AFM upon stretching the lactose-galectin 3 complexes according to embodiments of the present invention. Panel a shows a force peak for one specific binding event. Panel b shows a surface contact that did not result in observed binding and panel c shows nonspecific adhesion between the surface and AFM tip.

Typical force spectrograms obtained using this device are shown in FIGS. 3a-3c. In the absence of soluble ligand, force spectrograms corresponding to the rupture of noncovalent protein-ligand interaction are most commonly observed (FIG. 3a). The rupture force varies in magnitude from ~25 to 125 pN at extensions of greater than 10 nm. These rupture forces are comparable to the ones measured with AFM for avidin-biotin and various antibody-antigen systems (Florin 1994; Hinterdorfer, Raab et al. 1997; Wong 1998). Nonspecific adhesion and contact forces are also occasionally observed (FIG. 3b, 3c); these events are readily distinguished from specific binding events as they occur at extensions less than 10 nm. Presumably, these outcomes result from minimal implantation of the tip into the protein-coated surface and from electrostatic and/or van der Waals attraction between the tip and surface, respectively. Finally, a low level of nonspecific attachment of protein to the tip occurs, resulting in forces greater than 125 pN at extensions much greater than 10 nm, possibly involving the mechanical unraveling of galectin 3.

Figure 4:
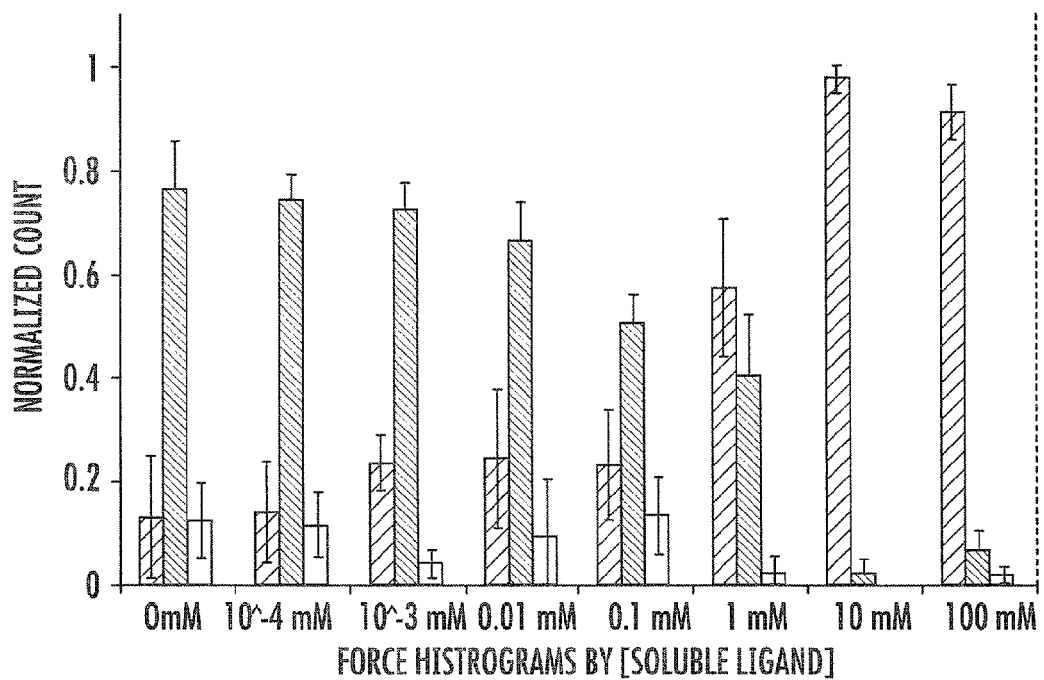
FIG. 4 illustrates force signatures, including force histograms obtained at varying concentrations of β-methyl lactoside according to embodiments of the present invention. Each histogram represents 350-800 collected force spectrograms. Data were binned: 0-25 pN, 25-125 pN, 125-200 pN.

Force spectroscopy measurements were carried out in binding buffer containing soluble β-methyl lactoside at concentrations ranging from 0 to 100 mM. At each concentration of soluble ligand, 350-800 force spectrograms were captured and analyzed. Force spectrograms collected using a blank coated tip were collected as a control. The data were binned; pulls resulting in rupture forces between 25 and 125 pN were scored as specific binding events while pulls resulting in rupture forces of greater than 125 pN were scored as nonspecific binding events. Pulls resulting in rupture forces of less than 25 pN and pulls resulting in forces at less than 10 nm extensions (ie. nonspecific adhesion and contact forces) were scored as non-binding events. Nonspecific adhesion and contact forces were not binned when they were coincident with specific forces at longer extensions. The normalized bin count bin was determined at each soluble ligand concentration and plotted as a function of soluble ligand concentration (FIG. 4). Random errors were evaluated by comparison of groups of 100 consecutive observations. The error bars in FIG. 4 represent one standard deviation from the mean normalized count for each bin.

Several groups have reported that the histidine hexapeptide-nickel(II) complex dissociates at forces within the range that is described as including specific interactions at loading rates comparable to those used here, and it is possible that the His-$Ni^{2+}$ interaction is ruptured, rather than the galectin-lactose pair (Conti, Falini et al. 2000; Kienberger 2000; Schmitt, Ludwig et al. 2000). The iron(III)-hexahis tag interaction (measured at 1 nm $ms^{-1}$ loading rate) displays a larger rupture force than that of nickel(II), (Conti, Falini et al. 2000) providing a ready means to distinguish the two events. Force spectrograms were collected using iron(III) in place of nickel (II) for surface immobilization of galectin 3. The data for each metal were parsed into 10 pN bins and the average rupture force calculated using a Gaussian fit. The average rupture forces (72 pN and 71 pN for $Ni^{2+}$ and $Fe^{3+}$ respectively) were substantially the same, which is consistent with a detection of the rupture force of the lactose-galectin 3 interaction.

Figure 5:
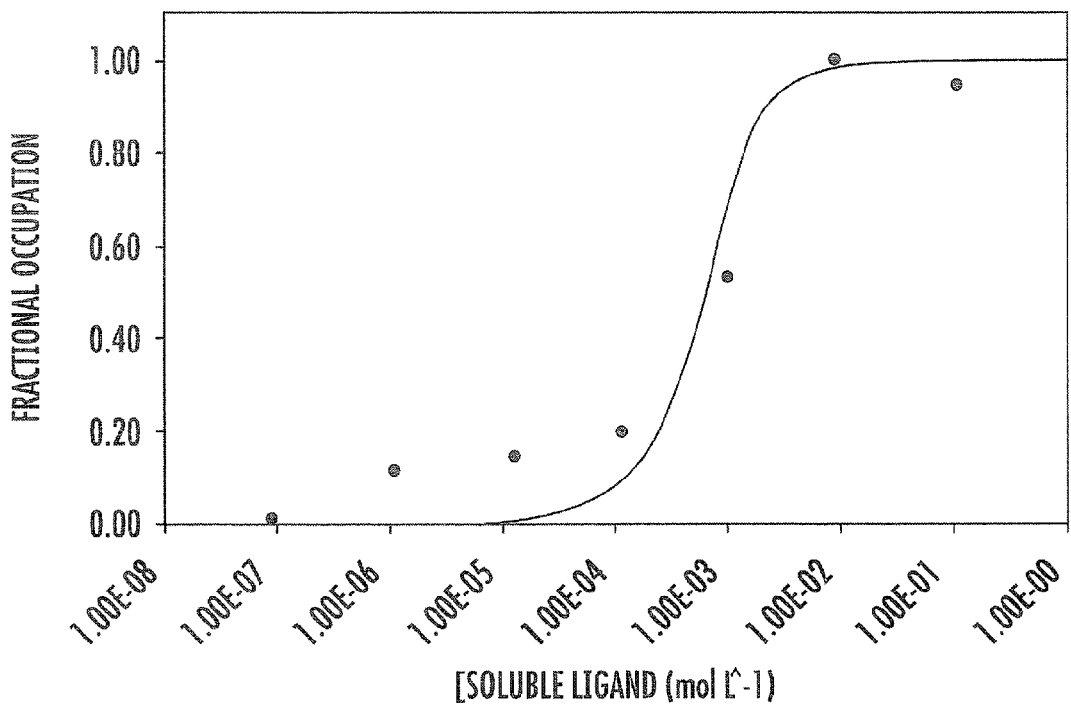
FIG. 5 is a graph plot of fractional occupancy of surface binding sites as function of soluble ligand concentration according to embodiments of the present invention. Data points represent the normalized count of the 0-25 pN bin divided by the normalized count over 0-125 pN. The data are normalized by scaling to the unity for the maximum value and subtracting the minimum value. The binding isotherm for an association constant of 6400±100, the affinity measured by isothermal titration calorimetry, is shown for comparison.

The normalized count of observed rupture forces varies with the concentration of soluble ligand. At low ligand concentrations, specific rupture forces are the predominant event, accounting for nearly 80% of all encounters. As the soluble ligand concentration increases, the frequency of specific rupture events diminishes with a concomitant increase in the frequency of null events, an observation consistent with competition between soluble and immobilized ligand for immobilized protein. A plot of the ratio of null events to specific binding events is shown in FIG. 5.

Figure 6:
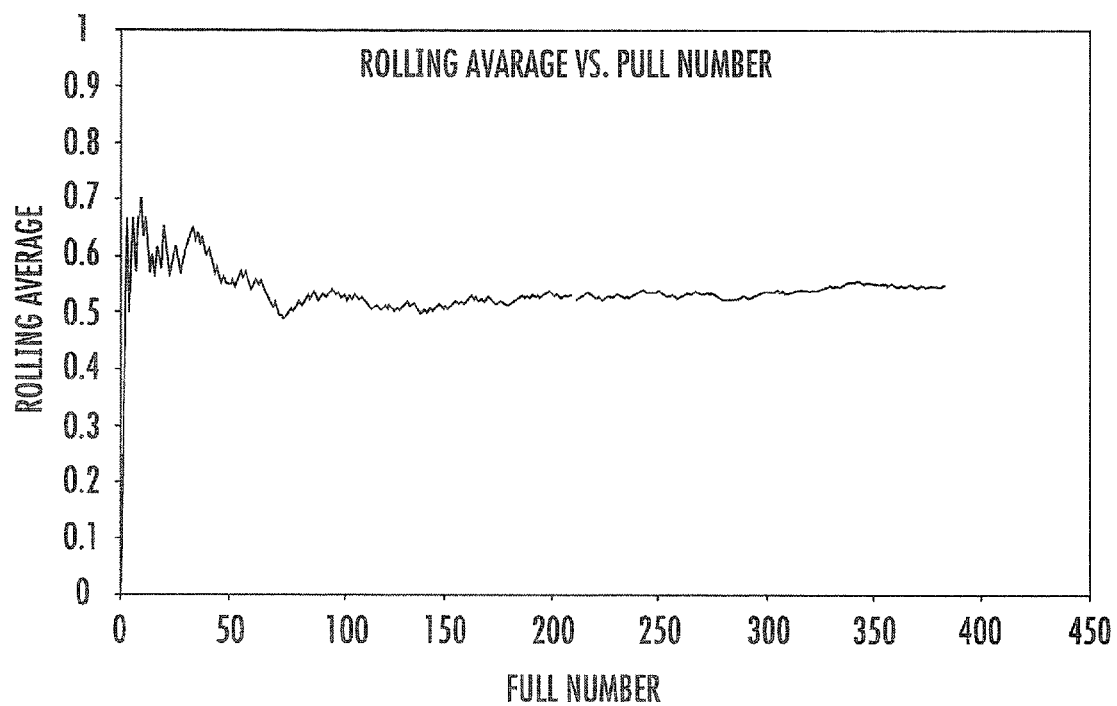
FIG. 6 is a graph of the rolling average of bound fraction as a function of pull number for a cantilever device according to embodiments of the present invention.

The number of "pulls" required to accurately determine the bound fraction was also considered (FIG. 6). A plot of the average fractional binding at 1 mM soluble ligand suggests that roughly 150 pulls are sufficient to accurately determine the bound fraction.

Figure 13:
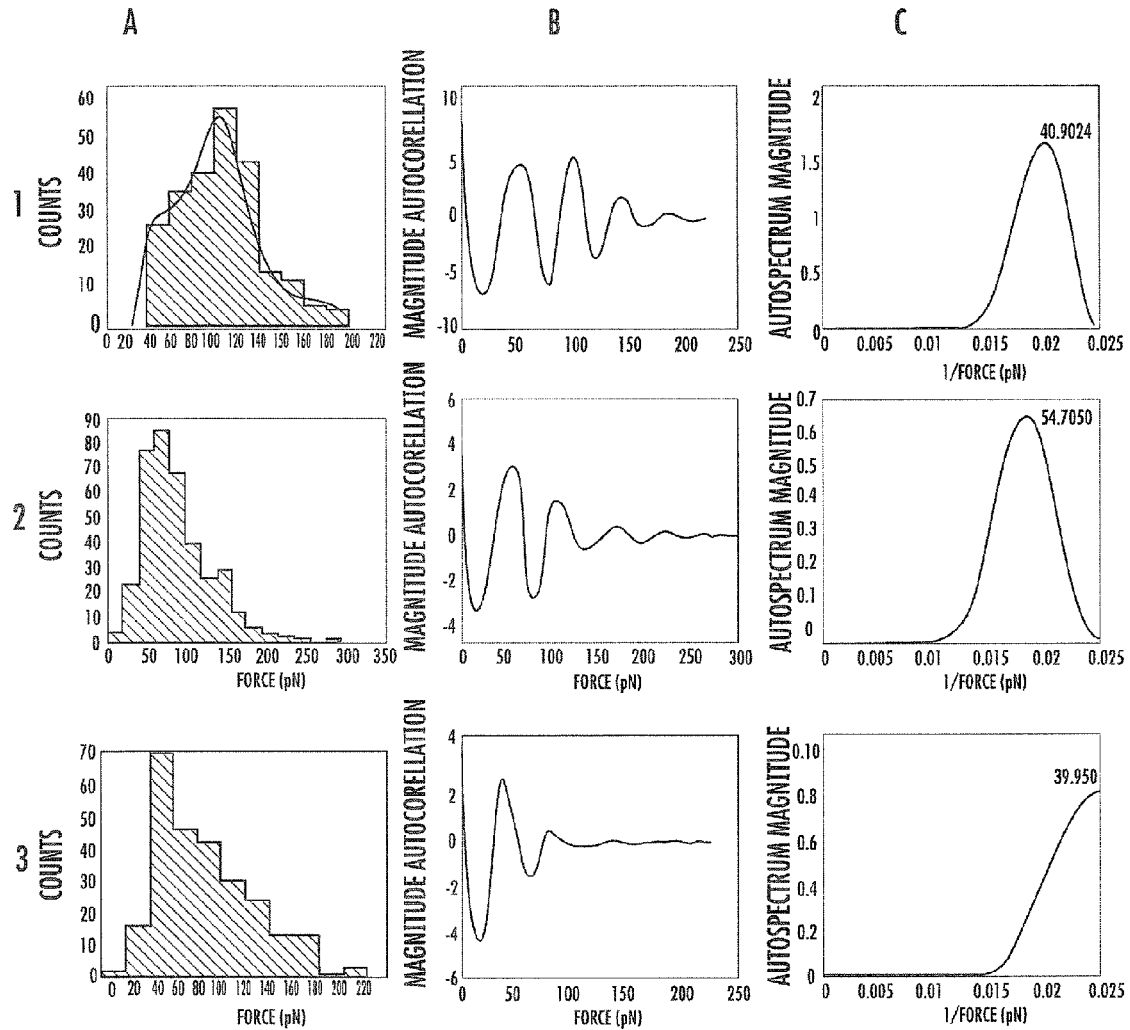
FIG. 13 are graphs illustrating (a) Histograms, (b) autocorrelation functions, and (c) power spectra for the ruptures immobilized lactose-gelactin 3 complexes in the precence of (1) no M soluble lactose, (2) $10^{-7}$ M soluble lactose and $10^{-5}$ M soluble lactose according to embodiments of the present invention.
Figure 14:
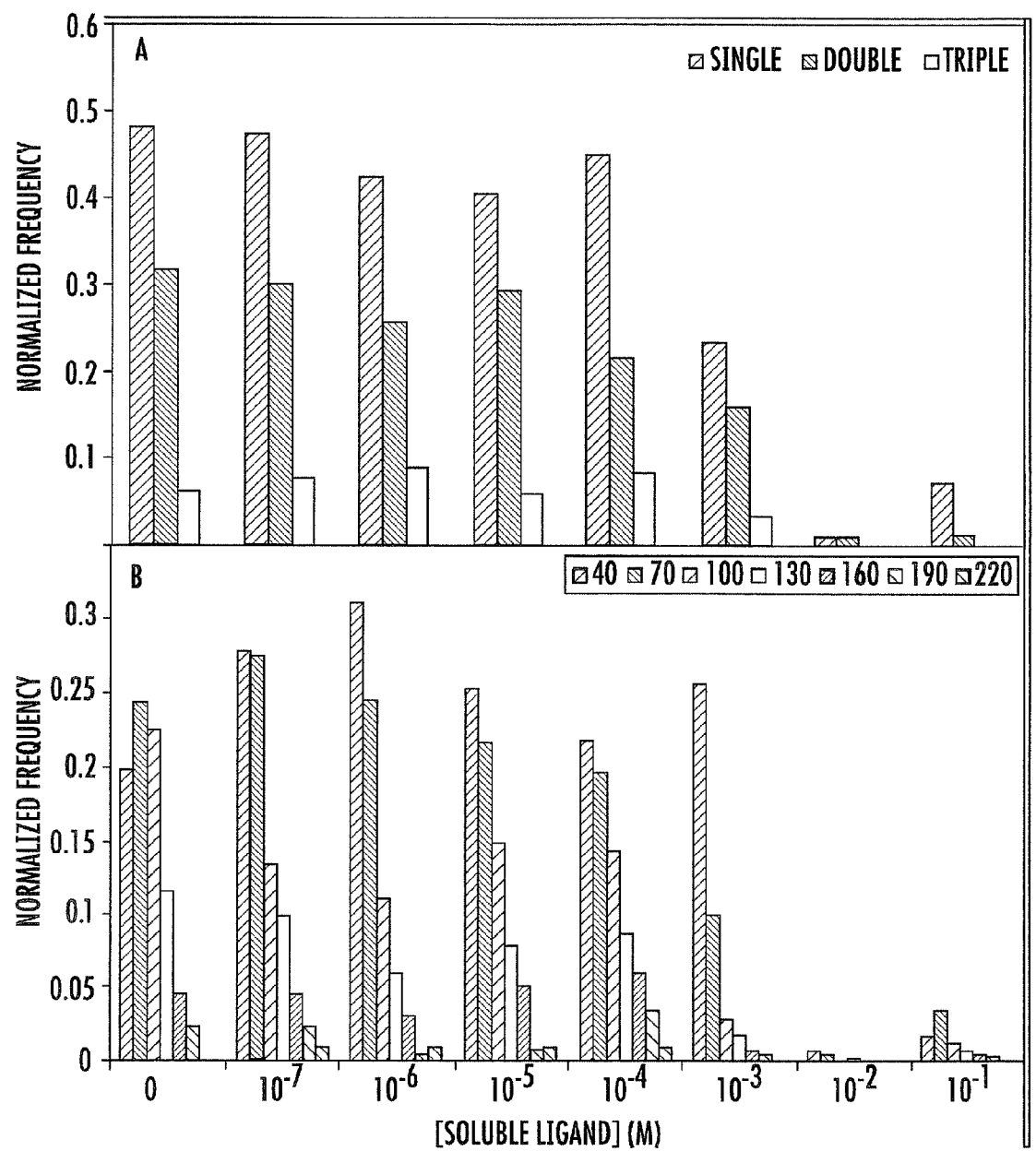
FIG. 14 are graphs illustrating the effect of soluble ligand on multivalency. (A) Bin breadths correspond to single multiples of complex formation. (B) Bar colors/shading relate the frequency of each type of attachment observed, only binding events are tallied, and bin counts are normalized to the total number of pulls collected at the concentration (binding+non-binding).

The Effect of Multivalency. An immobilization protocol produces tips and surfaces functionalized at a density that results in multiple protein-ligand complexes on each approach; simple calculation predicts ~13 interactions are feasible, given the cantilever design and the nature of the surface functionalization. Multivalency can have an effect on the determination of the probability of binding, and evaluation of this term can be made using knowledge of the total number of protein-carbohydrate interactions ruptured on each pull. Deconvolution of this value can be performed using knowledge of the force required to rupture a single interaction. The autocorrelation function is a convenient tool for identifying periodicity (Bendat & Piersol, 2000) and Florin and coworkers reported the use of such functions to observe the periodic nature in force-bin count histograms (Florin, 1994). Briefly, the histogram of bin counts as a function of rupture force was fit to a polynomial function and an autocorrelation function based upon the difference between the polynomial fit of the histogram evaluated at the center of the bin was subtracted from the actual histogram data (Florin, 1994; Marchand & Marmet, 1983). The periods observed in the autocorrelation function were then averaged to determine the fundamental period, which was equated with the fundamental rupture force of a single binding event at a fixed loading rate, an equality that assumes a linear relationship between valency and unbinding force. As described by Williams (Williams, 2003), this approach yields an underestimate of the fundamental binding force, because the rupture force for individual complexes in a multiply bound complex vary as the loading rate, a value not necessarily equivalent for multiple sequential unbindings. This correction, however, will be negligible for low (2-3) valent bindings, and small even at higher values and, for the purpose of this study, the approach yields a reasonable approximation. This approach can be extended by calculating the monomeric rupture force through the use of power spectra. The histogram bin spacing, $\Delta F$, is analogous to time in discrete-time signal processing, where the sample rate is computed from $1/\Delta t$ and the Nyquist frequency ($1/(2\Delta t)$) sets an upper limit to the frequency that can be resolved. The Fourier transform of the autocorrelation function produces an autospectrum, which is in turn used to determine the frequency of a periodic signal in the time domain. By analogy, $1/(2\Delta F)$ defines the upper bound for the "frequency" that can be resolved for the periodic signal from the force data. The microcantilevers used here afford a resolution of ~20 pN: this value may set a lower bound on the bin size, and the smallest force that can be resolved may be about, $2\Delta F$, or 40 pN. A polynomial fit was applied to the histogram compiled at each soluble ligand concentration: the order of the polynomial was selected so as to capture the best fit of the dominant peak and the remainder of the bins in the histogram. From this fit, an autocorrelation function was derived and a Fourier transform was computed to identify the fundamental force present in the data. One advantage of this approach is that derivation of the fundamental force is based on integration over all data in the autocorrelation function, as opposed to an average of the period observed from a limited number of data points. FIG. 13(1a) shows the force histogram in the absence of soluble ligand, fit to a ninth-order polynomial. The resulting autocorrelation function (FIG. 13 (1b)) shows obvious periodicity of ~50 pN. The corresponding autospectrum, obtained from the Fourier transform of the autocorrelation function (FIG. 13 (1c)) is consistent with this observation, showing a peak at 0.02 pN-1, suggesting a monovalent rupture force of 50±10 pN, or any integer factor of this value. The process was repeated in the presence of $10^{-7}$ and $10^{-5}$ M lactose. As expected, the addition of soluble ligand diminishes the probability of multiple binding events. Comparison of the histograms at 0, $10^{-7}$, and $10^{-5}$ M soluble ligand shows a shift in the maximum bin count from 100 to 60 to 40 pN, respectively. At $10^{-7}$ M soluble lactose, a fundamental period of 50 pN is again observed: at $10^{-5}$ M the fundamental period appears at 40 pN, the smallest period that can be resolved based on the Nyquist criterion for the sampled data set. Notably, the histogram continued to shift toward lower rupture forces as the concentration of soluble ligand increased. At $10^{-3}$ M, 242 of the 380 data points correspond to rupture forces at bins centered at 20 and 40 pN: these values fix the fundamental monovalent unbinding force. The 40 and 50 pN periods identified at lower soluble ligand concentrations are integer multiples of 20 and 25 pN, suggesting a fundamental unbinding force for a monovalent protein-ligand interaction of between 20 and 25 pN. This value is comparable to AFM values reported for the rupture of other lectin-carbohydrate interactions (Zhang, 2004), although a direct comparison of rupture forces may also depend on loading rate (Lo, 2001). A monomeric unbinding force of 20-25 pN suggests that tip-surface encounter in the absence of soluble ligand most commonly results in the formation of five or six bound complexes; accepting nonidealities of the system this value is in good agreement with the predicted maximum number of interactions.

IV. Exemplary Design and Fabrication of Microcantilevers

Design parameters for individual microcantilevers can be based on knowledge of non-covalent binding forces. The integration of the transducer within the overall sensor system can use electrical inputs and outputs to interface with the diagnostic device. Alternative methods of measuring the response of the microcantilever may also be used, including piezoresistive, piezoelectric, and optical techniques.

The number of times that the ligand attached to the microcantilever binds to a protein on the substrate surface can be ascertained. This enumeration can be achieved using various techniques, such as through repetitive interrogation with a single cantilever (as demonstrated above) or through single interrogation of an array of cantilevers to conduct a statistically meaningful ensemble of measurements simultaneously. The basic design of the microcantilever is the same for both sensor system concepts, and thus the design can be specified through a combination of analytical design and experimental testing using conventional AFM platforms to verify the design.

The microcantilever, which serves as a nano-electromechanical sensor, can be individually addressed, electrically or optically, to provide a measure of the dynamic response. The mechanical and geometric design parameters that define the microcantilevers can be based upon optimization of the dynamic response of the microcantilever. However, the alternative methods of transduction can be considered, and the method providing the best signal response for the lowest cost of integration can be selected. Standard optomechanical methods are an option, as integrated in the conventional AFM for quantifying microcantilever deflection; however, two electromechanical options may also be considered. One is a passive piezoresistive sensor and the other is an integrated active piezoelectric cantilever. Both have been successfully manufactured. According to embodiments of the present invention, a calibrated design of a piezoelectric array can be used for simultaneous actuation and sensing of single molecule interactions.

Piezoresistive sensors have been fabricated. These sensors contained high aspect ratios on the order of 500:1 (length: width) with resistances in the range of 10-50 kΩ. The devices were fabricated on SOI wafers with the piezoresistive layer formed in the upper silicon device layer and released by etching the buried oxide layer to form suspended beams. In some embodiments, sensors can be used that have much less stringent requirements with lower aspect ratios, and also lower overall device resistance for better force sensitivity.

Figure 7:
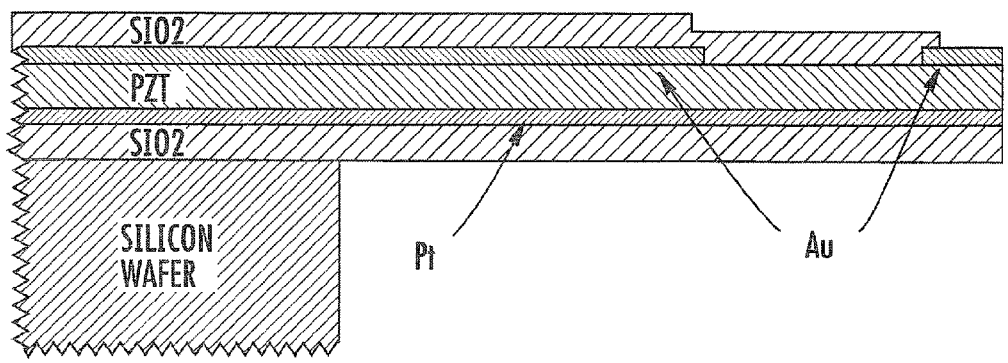
FIG. 7 is a process flow schematic for microfabrication of PZT active cantilever according to embodiments of the present invention.
Figure 8:
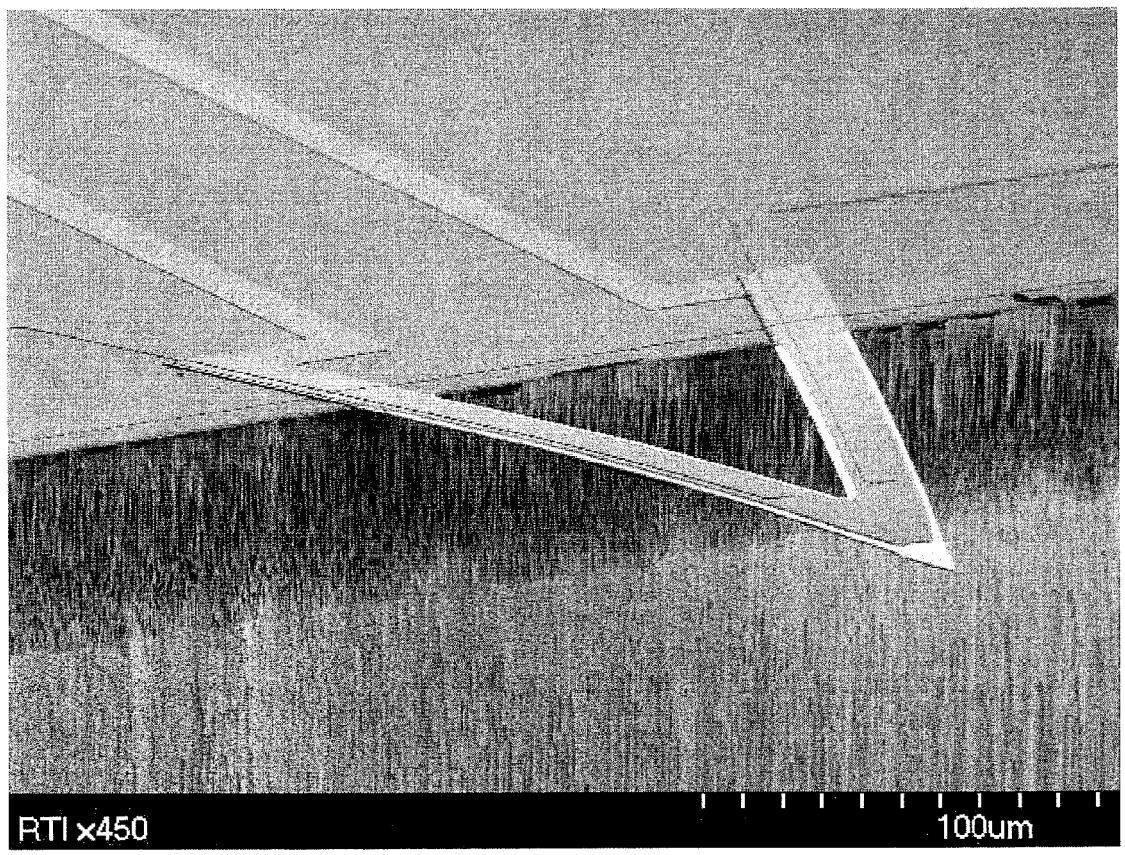
FIG. 8 is an SEM micrograph of a microfabricated PZT active cantilever with 150 μm length (from base to tip) and 15 μm wide legs, manufactured at RTI according to embodiments of the present invention.
Figure 9:
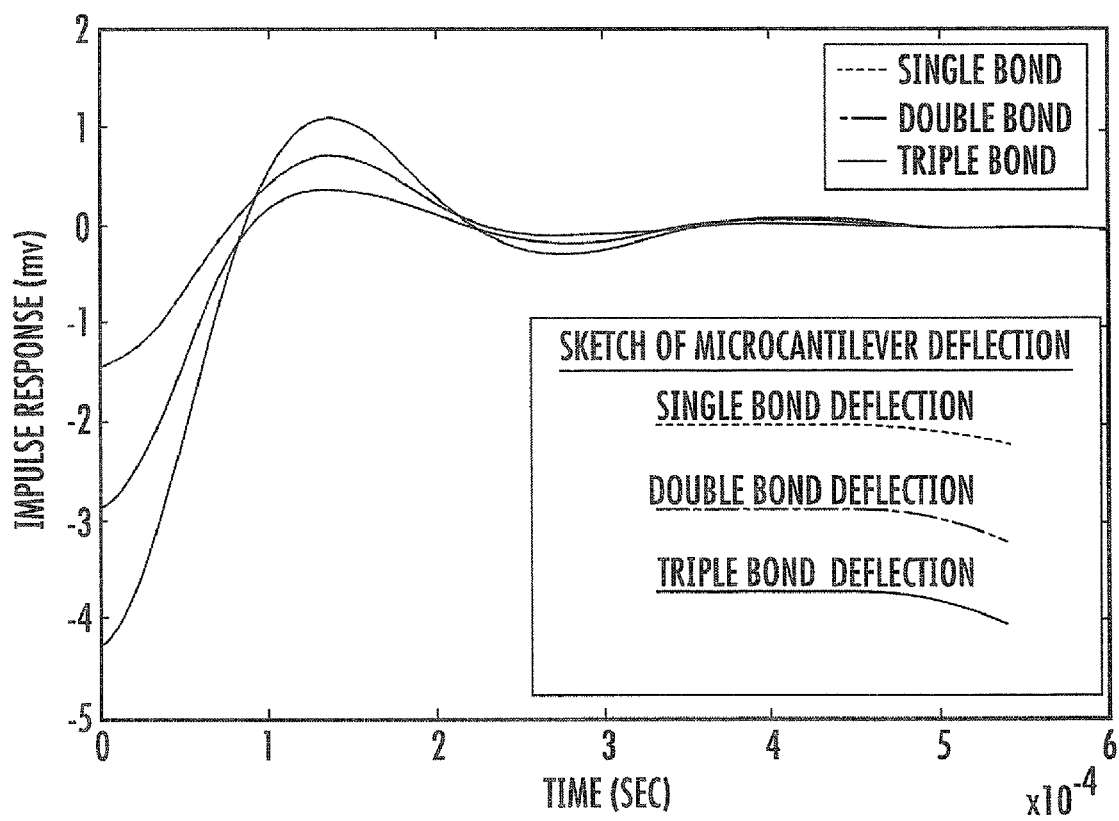
FIG. 9 is a graph of the impulse response as a function of time of a microcantilever for single bond, double bond, and triple bond according to embodiments of the present invention.

Piezoelectric microcantilever devices have been fabricated on thermally oxidized silicon wafers with the oxide layer forming the structural base of the cantilevers (shown in FIG. 7). A platinum bottom electrode was deposited by electron beam evaporation. For the piezoelectric layer, $Pb(Zr_{0.53}Ti_{0.47})O_3$ (PZT) was spin-coated from metal organic precursors and annealed at 700° C. The top electrode and antibody attachment pad were deposited by electron beam evaporation of gold and patterned using a liftoff method. A final layer of silicon dioxide was deposited using PECVD to serve as the top insulator. Using finite element modeling, the thickness of this top insulator was tuned to minimize curvature in the cantilevers (due to pre-stress). Without this top insulator, the cantilevers have a significant upward curl due to the combination of the compressive thermal oxide base layer and the tensile PZT and platinum layers. The top insulator was etched away at the cantilever tip in order to expose the gold antibody attachment site. Finally, the cantilevers were released from the silicon substrate using deep reactive ion etching (DRIE) of the silicon from the backside of the wafers. A scanning electron micrograph of one of the devices manufactured is illustrated in FIG. 8. The microcantilever illustrated is triangular; however, rectangular shaped microcantilevers can be manufactured as well. Devices have been fabrication with base-to-tip lengths of 150 µm-300 µm, leg widths of 20 µm-40 µm, and total thicknesses of 750 nm-1500 nm; however, other base-to-tip lengths may be used. This basic fabrication process serves as an example of the processes that can be employed in manufacturing an array of microcantilevers.

Final packaging of both types of cantilever devices can include passivation from the liquid sample environment. This may involve one of two methods including deposition of a thin (~1 µm) photoimageable silicone film before back side etch of the silicon substrate. Silicone has a very low modulus, so its effect on the spring constant of the cantilever may be negligible. The silicone is cured selectively with UV using a photolithography mask, so areas above the electrical bond pads (at the edge of the die) and the gold or silicon dioxide attachment pads can remain clear of the passivation coating. Electrodes for the piezoresistive and piezoelectric devices can be passivated. Following bonding of the electrical pads at the edge of the die to the control circuit, these areas can then be encapsulated with epoxy to prevent shorting of the leads in the liquid environment. For the piezoresistive devices, the back sides of the cantilevers can also need to be coated to passivate the exposed device layer silicon on the under side of the cantilever. This can be accomplished by depositing a thin (~50-100 nm) conformal PECVD silicon nitride layer on the back side of the wafer, which can also deposit through the etched windows onto the exposed silicon devices. The back sides of the piezoelectric devices can already be passivated by the silicon nitride cantilevers.

An alternative method includes deposition of a conformal PVD parylene coating on the cantilever structures after the back side silicon etch. This deposition can coat both sides of the cantilever devices. Parylene is an excellent moisture barrier and can seal the cantilever devices from the outside environment. Before parylene deposition, however, the electrical pads at the edges of the die can be masked off to prevent coating with parylene. Also the attachment pad at the tip can be masked off before deposition or exposed by selectively etching the parylene after deposition. Cantilevers can be designed with varied dimensions and different array sizes on each wafer in order to give a range of potential optimized structures for binding force measurement. Individual arrays can be diced from the wafers for testing.

Signal processing can be implemented on a digital signal processor (DSP), and the analog signals produced by the sensor system can be captured with an analog to digital converter. The DSP platform can serve as a rapid prototyping environment for integration and evaluation of software for final product design. Examples of platforms that are suitable for point-of-care diagnostics include a simple hardware interface. The interface can be constructed large enough to hold a cartridge, which can include the microcantilever array and associated electrical outputs. The hardware interface can be a stand-alone instrument and can contain the necessary drive electronics. The hardware interface can produce the output signals, which can be observed on the device or with a second device, such as a desktop or laptop computer. Various hardware/software interfaces can be developed and used interchangeably on the hardware interface. In other embodiments, the drive electronics and signal processing can be integrated onto a single integrated chip.

A. Threshold Force Sensing for Multiple Analytes

The sensor system can incorporate an array of microcantilevers, sufficient in number to provide a statistically significant result. As such, one can quantify the number of independent measures (i.e., microcantilevers) required for each target analyte. This can be accomplished as part of the sensor "design" and similar to the calibration of the force measurement through use of an atomic force microscope, statistical data can be obtained by repetitively contacting a surface with a single microcantilever and quantifying the binding events for each encounter. Thus, the use of an AFM for single axis force measurements can be used not only to calibrate the rupture force for a particular protein-ligand pair, but it can furthermore be used to determine the number of times the surface can be sampled to obtain a statistically significant result. The microcantilever array size can be based upon this result, a sensor array with approximately 150 microcantilevers was demonstrated to be acceptable (see FIG. 6); however, other suitable numbers of microcantilevers can be used. In particular embodiments, arrays can be configured to provide as few as hundreds of parallel measurements or two orders of magnitude greater or more. A dynamic measure of the force required to rupture a binding event can be used to measure binding events. This can simplify the design of the sensor array because it would otherwise be difficult to a) quantify the rupture force precisely or b) manufacture an array with a tolerance sufficient to maintain the separation between each microcantilever and the substrate concurrently. However, these problems may be reduced or avoided by imposing a tolerance that requires all microcantilevers to contact the substrate when the cartridges are inserted into the sensor system (FIG. 2).

Thus, as illustrated in FIG. 10, when the cartridges are inserted into the sensor system (step 1), the microcantilevers are forced into the substrate tip, covered with the desired sample containing the competitive target analyte. During step 2, an actuator is used to separate the microcantilever array from the substrate, and if specific binding events occur, then the microcantilevers can be deflected during the retraction. However, at some point during the retraction, the bond can rupture, and the force at which this rupture occurs can be recorded. The magnitude of this force is related to the deflection just prior to rupture. It can be viewed as the dynamic response to an initial condition (the initial condition being the deflection prior to rupture). For a known spring stiffness, the magnitude of the response can be monitored to register the event as a rupture due to specific binding or a "non-event" associated with a rupture due to non-specific binding. The registration of each event for the array of microcantilevers effectively produces a sample set of binary recordings which can be used to provide a quantitative measure of the target analyte concentration.

B. Actuation Design for Constant Loading

Engineering Design Capability. Commercial AFM heads are available, such as from Digital Instruments™. Commercially available AFM heads may accommodate a variety of microcantilevers.

Figure 11:
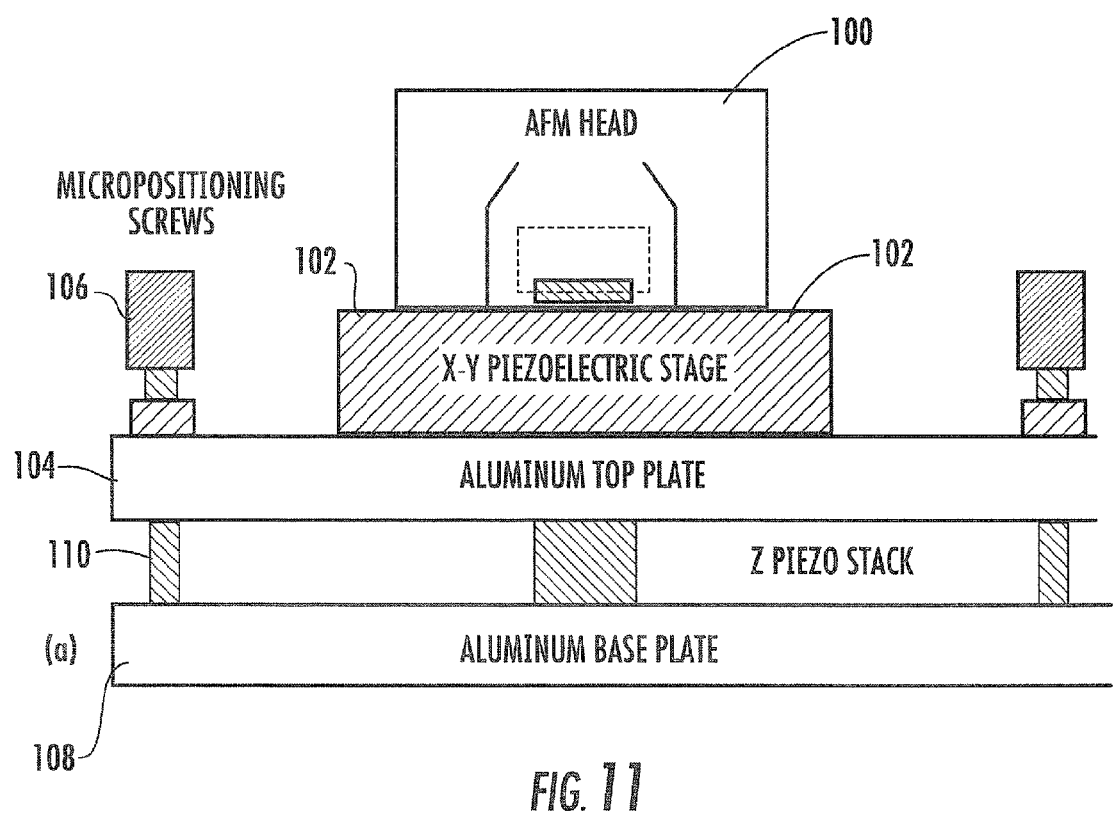
FIG. 11 is a schematic diagram of a scanning probe lithography platform according to embodiments of the present invention.

As illustrated in FIG. 11, a scanning probe lithography platform includes an AFM head 100, an x-y piezoelectric stage 102, an aluminum top plate 104, micropositioning screws 106, an aluminum base 108, and z piezoelectric stacks 110. The AFM head 100 contains a mounting bracket for the microcantilevers, a laser source, a 4-quadrant photodetector, alignment screws for the laser source and the head 100, and outputs the photodetector voltages. The AFM head 100 is mounted on the piezoelectric flexure stage 102 for nanopositioning in the x and y directions, manufactured by Piezomax™. The x-y positioning stage 102 is mounted to the aluminum top plate 104 containing three fine adjustment Newport™ positioning screws 106. This top plate 104 sits on the bottom base 108 that incorporates the Piezomax™ z-axis piezoelectric stack linear actuator 110. The sample surface is attached to the z-axis stack actuator 110 and the AFM head 100 containing the tip is moved in a horizontal plane above the sample with the x-y piezoelectric stage 102. The piezoelectric stack 110 and the flexure stage actuators 102 contain capacitive sensors that are able to detect position changes on the order of one nanometer. A high voltage drive signal is used to create motion in the x, y, and z directions. In order to maintain the piezoelectric actuators 110 at a specific location, proportional plus integral (PI) feedback control is used. This control scheme is digitally implemented through the use of a dSPACE™ DAQ PCI card with 16 bit resolution. During closed loop operation, the tip can be commanded to move in a three dimensional area of 70 μm by 70 μm by 12 μm with a resolution of ±5 nm in the x and y directions and ±0.5 nm in the z direction. Due to the open architecture of the software control interface, the instrument can be tailored to meet a wide-range of user-defined design criterion for single molecule spectroscopy and nanolithography.

Figure 12:
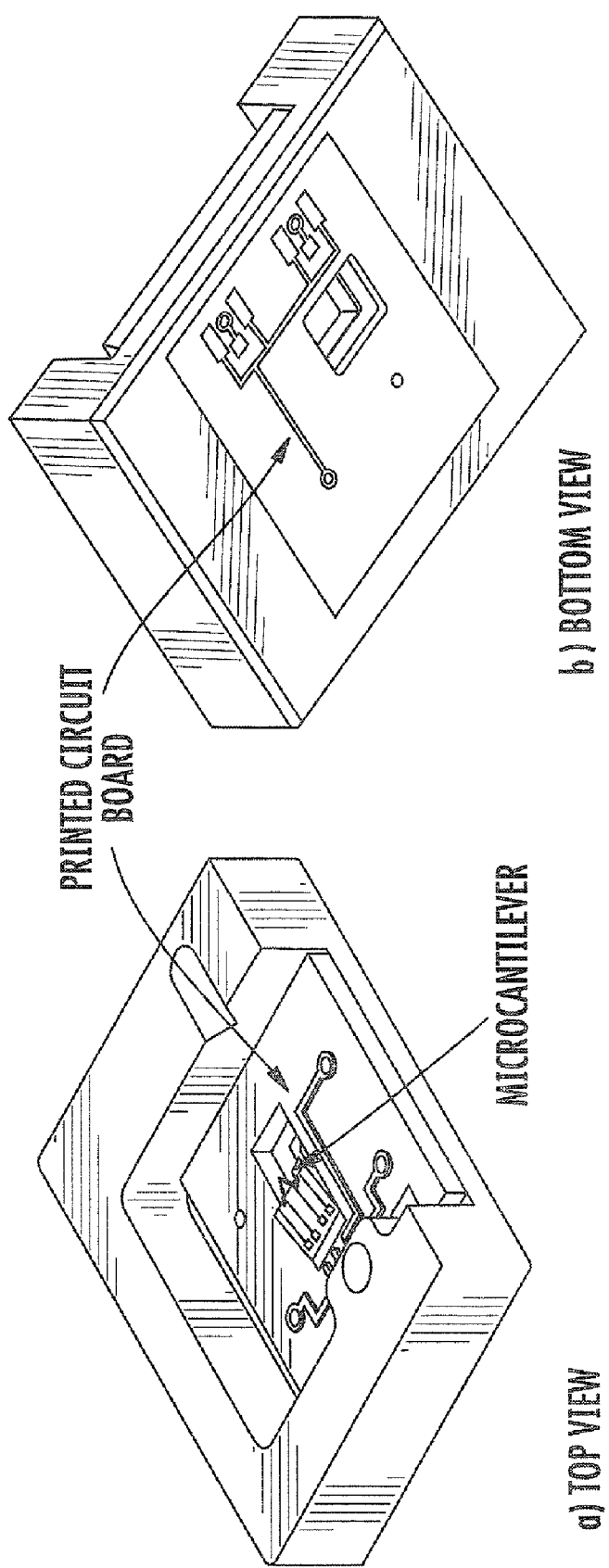
FIG. 12 is a schematic drawing of a custom AFM cartridge with printed circuit board designed to interface with microcantilevers designed for sensing applications according to embodiments of the present invention. a) is a top view of AFM cartridge; b) is a bottom view of AFM cartridge.

Some microcantilever designs for diagnostic sensing applications can include a cartridge that holds microcantilevers in the AFM head (for example, an AFM head is manufactured by Digital Instruments). Stereo lithography was used to build a basic prototype, and a printed circuit board was designed to interface the signal conditioning electronics with the microcantilever when mounted in the AFM. A drawing of the device is provided in FIG. 12. The ability to rapidly prototype hardware for instrument design enables tuning off-the-shelf instruments or design custom instruments for intended applications.

Actuator Design. An appropriate loading rate for the protein-ligand pair functionalized on each of the disposable cartridges can be determined for the threshold force sensor. In the laboratory design environment, the AFM is equipped with a piezoelectric transducer that is used to retract the substrate away from the microcantilever at a controlled rate. Such devices have become relatively cheap to manufacture in quantity and certainly serve as an option for actuation. Burleigh manufactures inchworm actuators that can be used to control position at sub-nanometer length scales. Various actuation devices can be used, including pneumatic actuation. In some embodiments, actuators separate the disposable sensor cartridges and can be a permanent part of the hand-held sensor system as illustrated in FIG. 2.

V. Development of a Troponin Sensor

Although a late marker of ACS (3 to 6 hours), troponin can be used to diagnose ACS. Accordingly, a cantilever-based sensor for Troponin I (TnI) can be used to diagnose ACS in a clinical setting. Various coupling strategies, optimal surface densities, and surface passivation from biofouling can be evaluated.

An anti-troponin/peptide binding system can be developed with an affinity near $10^{10}$ M$^{-1}$ that can facilitate analysis of troponin levels over the clinically relevant concentration range of 30 pM to 2 nM.

Values of serum TnI>2 µg/L (30 pM) generally indicate myocardial necrosis; accordingly, embodiments of the present invention can be based on an antibody-antigen pair with a $K_d$ of 300 pM. Hundreds of troponin monoclonal antibodies are commercially available and, in most cases, peptide mapping has been accomplished through SPOT peptide mapping protocols. In particular, Research Diagnostics, Inc. offers a range of antibodies specific to various peptide epitopes of tropoinin-I in milligram quantities (FIG. 1). Antibodies can be screened against peptide epitopes by isothermal titration microcalorimetry to identify binding pairs with appropriate affinities. Assuming affinities of $\geq 10^7$M$^{-1}$, each titration can require roughly 100 µg of antibody; affinities lower than this are of no use in this application. Peptide epitopes, generally ranging from 10-15 residues, can be synthesized manually using standard Fmoc solid-phase protocols. Milligram quantities can be more sufficient for affinity screening purposes. In some instances, affinities may be too high to determine by direct titration; in such circumstances, displacement techniques based on variants of target peptides can be used.

The effect of varying mechanisms of antibody attachment on reproducibility, affinity and stability of the bound antibody can be considered.

With an antibody-peptide system in hand, various mechanisms of binding antibody to the device surface can be used. The mode of surface attachment could conceivably affect affinity by restricting mobility or access to the binding domain: such effects have previously been demonstrated in affinity chromatography, surface plasmon resonance spectroscopy, and ELISA. (Wimalasena and Wilson 1991; Spitznagel, Jacobs et al. 1993; Lu, Smyth et al. 1996; Catimel, Nerrie et al. 1997) The mode of surface attachment can also affect the density of epitopes accessible to each tip-cantilever pair.

Oligo(ethylene glycol) surfaces can be prepared to avoid non-specific protein adsorption and biofouling; such monolayers are perhaps the best non-fouling surfaces reported to date. (Nath, Hyun et al. 2004) Surface fouling by biological samples can be broadly separated into two tasks: the non-specific adsorption of proteins, a process that occurs on microsecond to second time-scales, and the non-specific adsorption of cells, a process that occurs on minute to hour time-scales.

Various strategies for antibody immobilization can be examined, such as non-selective attachment of intact IgG by reaction through reactive lysine moieties, specific oriented immobilization of intact IgG by adhesion through adsorbed protein A, specific oriented immobilization of Fab fragments through a reactive cysteine sulfhydryl moiety. For example, a study related to antibody immobilization has recently been reported by Schoenfisch and coworkers. (Brogan, Shin et al. 2004; Brogan and Schoenfisch 2005)

One method of immunoglobin immobilization involves reaction of reactive lysine moieties. (Wagner, Hegner et al. 1996; Chowdhury and Luckham 1998; Stevens, Allen et al. 2000) Ethylene glycol/amine mixed monolayers can be prepared. Reactivity of these monolayers with immunoglobulin in the present of an α,ω-dialdehyde, such as glutaraldehyde, results in covalent attachment as either the imine or N,O-hemiaminal. Both linkages are in principle labile, although the imine moiety can be converted to the non-labile amine by treatment with NaCNBH$_3$. Alternatively, mixed monolayers of oligoethylene glycol and aldehyde-terminated absorbants can be prepared; such monolayers, recently been reported by Smith and coworkers, would facilitate direct adsorption of immunoglobulin. (Peelen and Smith 2005) Finally, N-hydroxysuccinamide ester/oligoethylene glycol mixed monolayers can be prepared. (Arisumi, Feng et al. 1998) Such surfaces can also react directly with free amino moieties of the immunoglobulin.

Although reactivity of immunoglobulin amino moieties is facile, it typically produces disordered and microheterogenous surfaces, since immunoglobulins possess multiple lysine residues throughout the entire IgG. Various strategies have been reported to achieve oriented monolayers of antibodies (Turková 1999), for example, immobilization through Protein A and thiol-based immobilization through Fab cysteine.

Protein A is a coat protein from *Staphylococcus aureus* that is released by proteolytic treatment. The protein has four high-affinity binding sites for the Fc domain of IgG antibodies and, as a result, has found considerable utility in various chromatographic and analytical applications. (Hjelm, Hjelm et al. 1972; Langone 1982) More recently, Protein A was used to specifically orient antibodies on a silicon nitride AFM tip. (Brogan, Shin et al. 2004) Mixed monolayers of both aldehyde/oligoethylene glycol and amine/ethylene glycol can be prepared as described above. Protein A can be bound to these surfaces either directly (aldehyde surfaces) or through a dialdehyde spacer (amine surfaces). The effect of covalent fixing in both cases by treatment with NaCNBH$_3$ can be considered. Following adsorption of Protein A, the reactive surface can be exposed to anti-troponin IgG monoclonal antibodies. The effect of covalent fixing of antibody to protein A can be considered; such bonding has previously been achieved with various cross-linking reagents, including carbodiimides and dimethyl suberimide.

The utility of F(ab') fragments of anti-troponin monoclonal antibodies can also be used. Proteolytic digestion of IgG with immobilized pepsin cleaves the F(ab') fragment from the Fc domain, leaving a single reactive cysteine moiety distal to the combining domain. Fc domain is readily removed by Protein A chromatography, and low-molecular weight impurities are removed by dialysis. Mixed oligo(ethylene glycol) monolayers can be prepared, which display electrophilic maleimides as described above and couple reactive F(ab') fragments directly to the surface.

The peptide epitope identified above can be bound to the apposing surface as a mixed oligo(ethylene glycol) monolayer. Both N- and C-terminal bound peptides can be prepared, in the former case by attachment through mercaptoundecanyl hexa(ethylene glycol)acetic acid, and in the latter case by direct esterification to 1-undecen-11-yl oligo(ethylene glycols) following straightforward modifications of the protocols described herein. Peptides can be linked directly or indirectly to surface monolayers; in some cases, such as if affinities are significantly lower than expected based on calorimetric studies, short oligo(ethylene glycol) tethers can be introduced.

In all cases the effect of modification can be determined by competitive assay with either TnI or soluble peptide. TnI is readily available from various vendors, and soluble peptide in the quantities required here (mg) can be prepared by standard solid-phase approaches. The assay can be conducted on the single axis force spectrometer described above. 150 pulls can be used in each instance; this experiment can be conducted during 2-3 hours.

The interacting surfaces here have radii of roughly 50 nM; complete coverage of both surfaces with antibody and peptide could conceivably result in interactions involving tens of binding events. Dilution of antibody and/or peptide can diminish the average number of interactions, providing a distribution of potential binders. The effect of the number of binding partners on the activity of the device by systematically diluting both peptide and protein in blank oligo(ethylene glycol) disulfide can be performed.

VI. Exemplary Sensor Systems

In general, an analytical device can be more sensitive to analyte concentrations where the analyte concentration is ± one log from the dissociation constant for the bound pair. Accordingly, a binding system may be developed and optimized for a given relevant concentration range. In many instances it may be necessary to assay analytes at significantly different concentrations. For example, while serum glucose concentrations are in the millimolar range, many protein markers are present in sub-nanomolar concentrations. One advantage of the cantilever platform is that the dynamic range of each analyte is independently determined by the nature of the bound ligand/bound protein pair. To extend the performance of the cantilever platform in the simultaneous evaluation of multiple analytes at widely varying concentrations, a single device containing binding systems to detect analytes at $10^{-4}$, $10^{-10}$, and $10^{-14}$ M concentrations can be construed. This device can also determine how the affinity of the interacting species affects the operation of the device, if at all.

Our original model system using lactose-galectin 3 binds with a bulk solution phase affinity of roughly $10^4$ $M^{-1}$. Systems with affinities significantly higher than our initial model can be added, such as biotin-streptavidin ($K_a \sim 10^{14}$ $M^{-1}$) and dihydrofolate reductase-methotrexate ($K_i \sim 10^{10} M^{-1}$). In both instances, the complete native ligand can be bound to the cantilever tip and the affinity for immobilized protein can be determined through competition experiments as described above using soluble ligand. To extend the utility of the cantilever-based binding device, analogues of the native ligand with diminished binding activities can be prepared. In some embodiments, the device can measure binding affinities from $10^4$ to $10^{15}$ $M^{-1}$.

Dihydrofolate Reductase/Methotrexate. Dihydrofolate reductase (E.C. 1.5.1.3) is a ubiquitous monomeric protein of 159 residues that reduces 7,8-dihydrofolate to 5,6,7,8-tetrahydrofolate with the concomitant oxidation of NADPH. A detailed kinetic mechanism for the transformation involving a series of conformational reorientations has been described by several researchers (Warren et al., 1991; Falzone et al., 1994; Sawaya & Kraut, 1997; Cannon et all, 1997; Rajagopalan et al, 2003). At neutral pH, rate determining product dissociation follows NADPH replacement of the oxidized cofactor, while at high pH hydride transfer becomes rate limiting. Tetrahydrofolate is a critical cofactor in the one-carbon biosynthesis of several purines, thymidylate, and amino acids. Thymidylate, in turn, is a key cellular intermediate in the synthesis of DNA and, as a result, DHFR has been exploited as a therapeutic target for rapidly dividing cells, including tumors and bacterial infections. Myriad small molecule inhibitors of the enzyme have been developed, including the antibacterial agent trimethoprim and the *Plasmodium* specific inhibitors pyrimethamine and cycloguanil. By far the most widely used antifolate chemotherapeutic is methotrexate ((Graffner-Nordberg et al., 2000; Subramanian & Kaufman, 1978; Waltham et al., 1988).

Wild-type human DHFR is commercially available (Quiagen) between BamHI and BglII restrictions sites in the pQE-16 vector. The modified protein can be overexpressed in BL21(de3) cells and purified by affinity chromatography over a methotrexate affinity column (Marszal & Scouten, 1996). The affinity of DHFR for methotrexate is significantly greater than that of galectin 3 for lactose; although a true $K_a$ for methotrexate has not been reported, it shows a sub-nanomolar $K_i$. With such tight binding, adhesion of protein to the solid support through chelation of hexaHis tags to surface-bound $Ni^{2+}$ can likely be ineffective, since pulling can almost certainly disrupt metal chelation rather than the methotrexate-DHFR interaction. Accordingly, DHFR can be covalently bound to surfaces by thiol adhesion to gold surfaces. A derivative of DHFR suitable for this purpose has been reported (Iwakura & Kokubu, 1993; Vigmond et al., 1994). Briefly, a double mutant of DHFR (Cys85Ala/Cys152Ser) was prepared; this protein shows catalytic activity essentially equivalent to native protein. A cysteine was then introduced to the C-terminus, facilitating adsorption onto a gold surface. This protocol can be utilized here, providing covalently bound DHFR.

The synthesis of methotrexate and its derivatives is below (Scheme 2) (Graffner-Nordberg et al., 2000).

Scheme 2

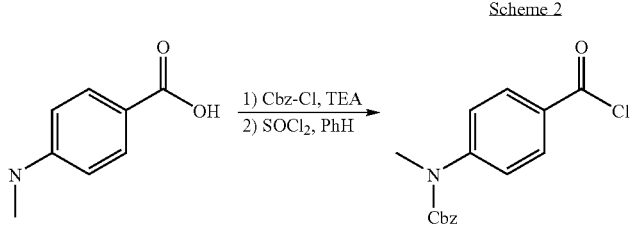

-continued

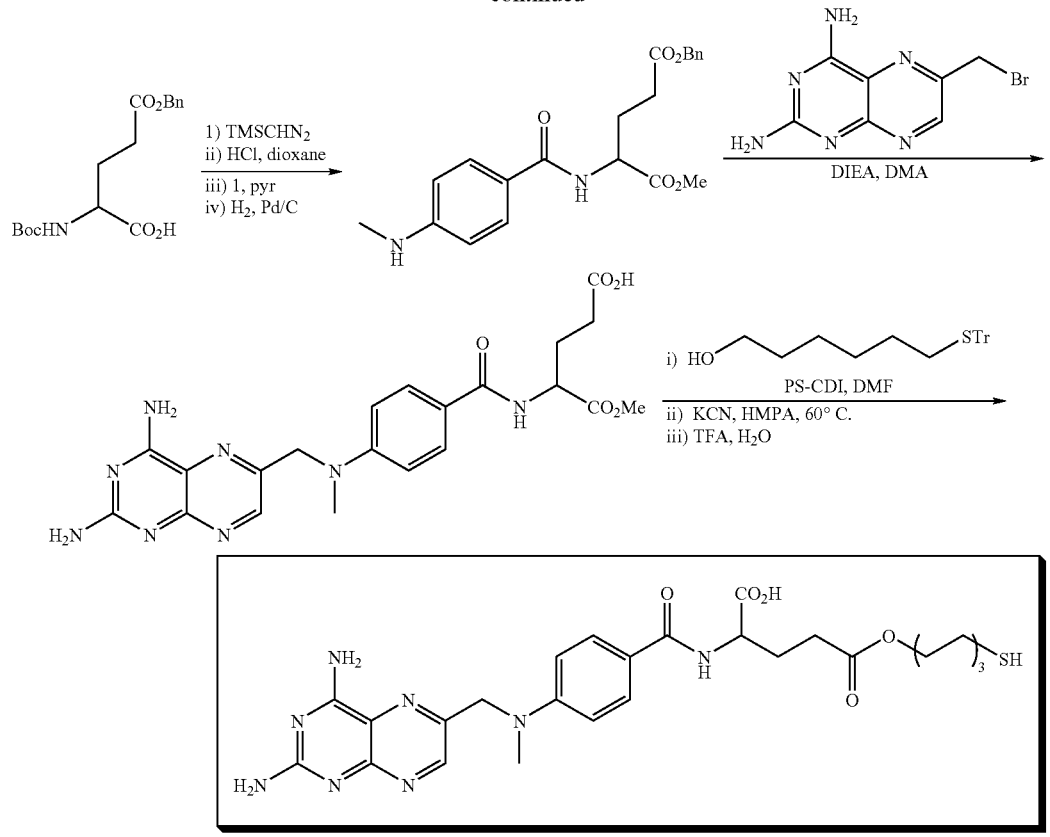

Briefly, ω-protected glutamic acid is acylated with monomethyl p-aminobenzoic acid. This fragment is coupled with diamino-6-(bromomethyl)quinazoline to produce the key diaminopteridine core. The crystal structure of myriad DHFRs have been solved bound to methotrexate (Whitlow et al., 1997; Hansch, 1982a; Hansch et al., 1982b). Uniformly, these structures show strong contacts between the diaminopteridine core, with a small number of important contacts between the benzoic acid linker. The glutamic acid moiety makes few contacts with the protein and is largely accessible to solvent. A wide variety of affinity resins are commercially available that link methotrexate to a solid support through the glutamate ω-carboxyl moiety, further suggesting this residue might be modified without deleterious effect on binding. Accordingly, methotrexate analogues bearing reactive sulfhydryl residues linked through the terminal glutamate residue can be produced.

Biotin/Streptavidin. Biotin (vitamin H) is a water soluble vitamin necessary as a cofactor for enzymes involved in carboxylation reactions, for example pyruvate decarboxylase and acetyl coenzyme A carboxylase. Avidin is a tetrameric glycoprotein of found at roughly 0.05% in egg white. The avidin-biotin binding system has been used extensively in protein science and enzymology because of the remarkably high affinity ($K_a$ $10^{13}$-$10^{15}$ $M^{-1}$). Unfortunately, microheterogeneity of the oligosaccharide chain and non-specific adsorption of avidin limit its utility. Streptavidin is a closely related protein isolated from the *Streptomyces avidinii*. Streptavidin shares with avidin an exceptional affinity for biotin but, isolated from a bacterial source, contains no carbohydrate. This modification abolishes both microheterogeneity and non-specific binding, and streptavidin is an important reagent in modern molecular biology. The protein is available from several commercial sources and has been cloned by Sano and Cantor (1990).

Because of the strength of the biotin-strepavidin complex, non-covalent association of the protein is again inappropriate. Accordingly, protein can be attached to the gold surface using the covalent strategy reported by Cantor and coworkers (Reznik et al., 2001). Briefly, a tether containing a unique cysteine was incorporated at the C-terminus of streptavidin. This tether (Gly-Gly-Ser-Gly-Cys-Pro) ensures that protein coupled to a gold surface through the cysteine orients in an extended, active conformation. Because streptavidin contains no other cysteines, this methodology produces active, monodisperse, highly ordered covalently bound material. Numerous other methodologies for covalent binding of streptavidin to surfaces have been reported (Yuan et al, 2000; Florin et al., 1994; Lee et al., 1994; Wong et al., 1999).

Biotin can be immobilized through carboxy terminus using standard chemistry. Reduction of the carboxyl terminal to the alcohol and conversion to the sulfhydryl facilitates direct coupling to gold surfaces. Alternatively, biotin can be linked via amide, ether or thioether linkages, again through the pendant alkyl terminus, to spacers of varying length, flexibility and hydrophobic character. A series of modified biotins with diminished binding affinities may be prepared that can bring the range of affinities probed into contact with the methotrexate DHFR system (Scheme 3) (Corey & Mehrotra, 1988; Baggiolini et al., 1982; Chavan et al., 2001; Field, 1978).

Scheme 3

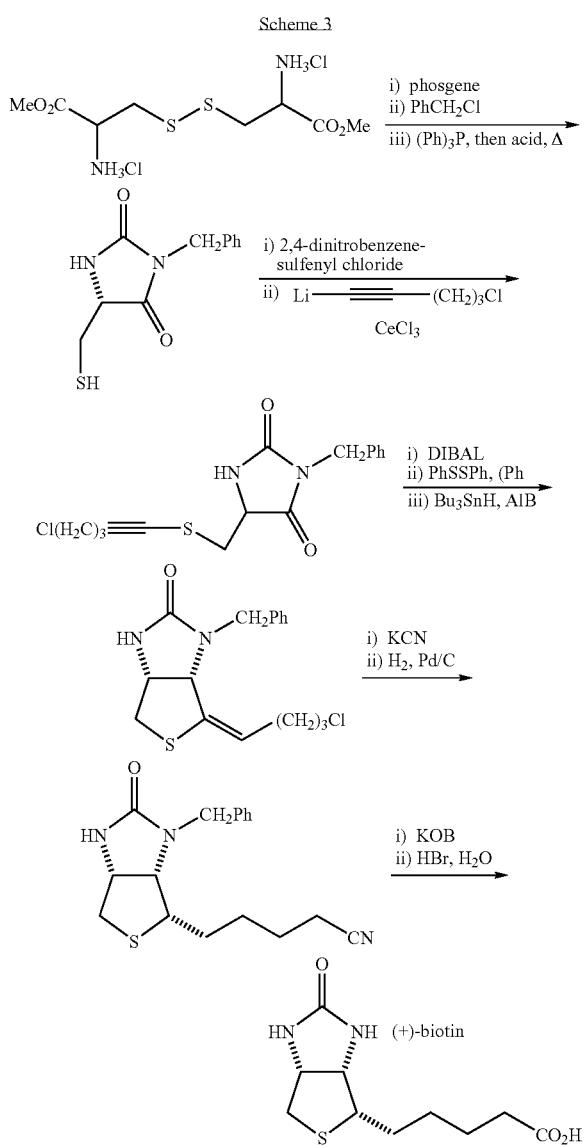

The amido nitrogens of the urea linkage can be alkylated; this modification with reagents as small as methyl through as large as isopropyl should diminish the affinity sufficiently. Various syntheses of biotin have been reported from cysteine, and modifications of these routes can facilitate ready access to derivatives with altered stereochemistry (D-versus L-cysteine), enlarged ring size (homocysteine versus cysteine) and variable length spacers. These modifications can diminish the affinity of soluble ligands to the level that they contact the DHFR/methotrexate system.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

REFERENCES

Alpert, J. S., K. Thygesen, et al. (2000). "Myocardial infarction redefined—A consensus document of the Joint European Society of Cardiology/American College of Cardiology Dommittee for the redefinition of Myocardial Infarction." J. Am. Coll. Cardiol. 36: 959-969.

Antczak, C., B. Bauvois, et al. (2001). "A new acivicin prodrug designed for tumor-targeted delivery." Bioorganic & Medicinal Chemistry 9(11): 2843-2848.

Antman, E. M., M. Cohen, et al. (2000). "The TIMI risk score for unstable angina/non-ST elevation MI. A method for prognostication and therapeutic decision making." JAMA 284: 835-842.

Apple, F. S., A. H. B. Wu, et al. (2005). "Future biomarkers for detection of ischemia and risk stratification in acute coronary syndrome. Report of the Committee on Standardization of Markers of Cardiac Damage of the IFCC." Clin. Chem. 51: 810-824.

Arisumi, K., F. Feng, et al. (1998). "Functionalization of Polymer Langmuir-Blodgett Films Using Active Ester Groups." Langmuir 14: 5555-5558.

Bendat, J. S., Piersol, A. J. (2000). "Random Data: Analysis & Measurement Procedures." Wiley, New York.

Blankenberg, S., H. J. Rupprecht, et al. (2003). "Plasma concentrations and genetic variation of matrix metalloproteinase 9 and prognosis of patients with cardiovascular disease." Circ. 107: 1579-1585.

Brogan, K. L. and M. H. Schoenfisch (2005). "Influence of antibody immobilization strategy on molecular recognition force microscopy measurements." Langmuir 21: 3054-3060.

Brogan, K. L., J. H. Shin, et al. (2004). "Influence of surfactants and antibody immobilization strategy on reducing nonspecific protein interactions for molecular recognition force microscopy." Langmuir 20: 9729-9735.

Brunwald, E., E. M. Antman, et al. (2002). "ACC/AHA guideline update for the management of patients with unstable angina and non-ST-segment elevation myocardial infarction. A report of the American College of Cardiology/American Heart Association task force on practice guidelines." J. Am. Coll. Cardiol. 40: 1366-1374.

Buffon, A., L. M. Biasucci, et al. (2002). "Widespread coronary inflammation in unstable angina." N. Engl. J. Med. 347: 5-12.

Catimel, B., M. Nerrie, et al. (1997). "Kinetic analysis of the interaction between the monoclonal antibody A33 and its colonic epithelial antigen by the use of an optical biosensor. A comparison of immobilisation strategies." J. Chromatograph. A 776: 15-30.

Chowdhury, P. B. and P. Luckham (1998). "Probing recognition process between an antibody and an antigen using atomic force microscopy." Colloids Surf., A 143: 53-57.

Conti, M., G. Falini, et al. (2000). "How strong is the coordination bond between a histidine tag and Ni-nitrilotriacetate? An experiment of mechanochemistry on single molecules." Angewandte Chemie-International Edition 39(1): 215-218.

Corrie, J. E. T. (1994). "Thiol-Reactive Fluorescent-Probes for Protein Labeling." Journal of the Chemical Society-Perkin Transactions 1(20): 2975-2982.

de Winter, R. J., R. W. Koster, et al. (1995). "Value of myoglobin, troponin T, and CK-MBmass in ruling out an acute myocardial infarction in the emergency room." Circ. 92: 3401-3407.

Dill, K. A, Bromberg, S., (2002). "Molecular Driving Forces: Statistical Thermodynamics in Chemistry and Biology. (Garland, N.Y.).

Evans, E. and K. Ritchie (1997). "Dynamic strength of molecular adhesion bonds." Biophysical Journal 72(4): 1541-1555.

Florin, E. L., Rief, M., Lehmann, H., Ludwig, M., Dornmair, C., Moy, V. T. & Gaub, H. E. (1995). "specific molecular interactions with the atomic force microscope." Biosensors and Bioelectronics 10: 895-901.

Florin, E. L. M., Vincent T.; Gaub, Hermann E. (1994). "Adhesion forces between individual ligand-receptor pairs." Science 264(5157): 415-417.

Gibbons, R. J., K. Chatterjee, et al. (1999). "ACC/AHA/ACP-ASIM guidelines for the management of patients with chronic stable angina: A report of the American College of Cardiology/American Heart Association Task Force of Practice Guidelines." J. Am. Coll. Cardiol. 33: 2092-2197.

Goldman, L., E. F. Cook, et al. (1988). "A computer protocol to predict myocardial infarction in emergency department patients with chest pain." N. Engl. J. Med. 318: 797-803.

Hafizovic, S., D. Barrettino, et al. (2004). "Single-chip mechatronic microsystem for surface imaging and force response studies." Proceedings of the National Academy of Sciences of the United States of America 101(49): 17011-17015.

Heeschen, C., S. Dimmeler, et al. (2004). "Prognostic value of placental growth factor in patients with acute chest pain." JAMA 291: 435-441.

Heeschen, C., S. Fichtlscherer, et al. (2003). "Pregnancy-associated plasma protein A (PAPP-A) plasma levels independently predict outcome in troponin negative patients with acute coronary syndrome." Circ. 108 (Supp. IV): 470.

Heeschen, C., B. U. Goldmann, et al. (1999). "Evaluation of a rapid whole blood ELISA for quantification of troponin I in patients with acute chest pain." Clin. Chem. 45: 1789-1796.

Hinterdorfer, P., A. Raab, et al. (1997). "Single antibody-antigen recognition events measured by atomic force microscopy." European Journal of Cell Biology 74: 71-71.

Hjelm, H., K. Hjelm, et al. (1972). "Protein a from *Staphylococcus aureus*. Its isolation by affinity chromatography and its use as an immunosorbent for isolation of immunoglobulins." FEBS Lett. 28: 73-76.

Houseman, B. T., E. S. Gawalt, et al. (2003). "Maleimide-functionalized self-assembled monolayers for the preparation of peptide and carbohydrate biochips." Langmuir 19(5): 1522-1531.

Kai, H., H. Ikeda, et al. (1998). "Peripheral blood levels of matrix mealloprteases-2 and -9 and tissue inhibitor of metalloproteinase-1 are increased in coronary circulation in patients with acute coronary syndrome." J. Am. Coll. Cardiol. 32: 368-372.

Kartha, K. P. R. and H. J. Jennings (1990). "A Simplified, One-Pot Preparation of Acetobromosugars from Reducing Sugars." Journal of Carbohydrate Chemistry 9(5): 777-781.

Kienberger, F. K., Gerald; Gruber, Hermann J.; Pastushenko, Vassili Ph.; Riener, Christian; Trieb, Maria; Knaus, Hans-Gunter; Schindler, Hansgeorg; Hinterdorfer, Peter (2000). "Recognition force spectroscopy studies of the NTA-His6 bond." Single Molecules 1(1): 59-65.

Kontos, M. C., F. P. Anderson, et al. (1999). "Early diagnosis of actue myocardial infarction in patients without ST-segment elevation." Am. J. Cardiol. 83: 959-969.

Langone, J. J. (1982). "Applications of immobilized protein A in immunochemical techniques." J. Immunol. Methods 55: 277-296.

Lee-Lewandrowski, E., D. Corboy, et al. (2003). "Implementation of a point-of-care satellite laboratory in the emergency department of an academic medical center." Arch. Lab. Path. Med. 127: 456-460.

Lo, Y-S, Zhu, Y-J, Beebe, T. P. (2001). Langmuir 17:3741-3748.

Lu, B., M. R. Smyth, et al. (1996). "Oriented immobilization of antibodies and its applications in immunoassays and immunosensors." Analyst 121: 29R-32R.

Lund, J., Q. P. Qin, et al. (2003). "Circulating pregnancy-associated plasma protein A predicts outcome in patients with acute coronary syndrome but no troponin I elevation." Circ. 108: 1924-1926.

Mammen, M., Choi, S. K., Whitesides, G. M. (1998). Angew Chem Int Ed Engl 37:2755-2794.

Mammen, M., Shakhnovich, E. I., Whitesides, G. M. (1998). J Org Chem 63:3168-3175.

Marantz, P. R., M. C. Kaplan, et al. (1990). "Clinical diagnosis of congestive heart failure in patients with acute dyspnea." Chest 97: 776-781.

Marchand, P., Marmet, L. (1983). Rev Sci Instrum 54:1034-1041.

Nath, N., J. Hyun, et al. (2004). "Surface engineering strategies for control of protein and cell interactions." Surf. Sci. 570: 98-110.

Oh, S., K. Foster, et al. (2000). "Use of a dual monoclonal solid phase and a polyclonal detector to create an immunoassay for the detection of human cardiac troponin I." Clin. Biochem. 33: 255-262.

Page, M. I., Jencks, W. P. (1971). Proc Natl Acad Sci USA 68:1678-1683.

Palegrosdemange, C., E. S. Simon, et al. (1991). "Formation of Self-Assembled Monolayers by Chemisorption of Derivatives of Oligo(Ethylene Glycol) of Structure Hs(Ch2)11(Och2ch2)Meta-Oh on Gold." Journal of the American Chemical Society 113(1): 12-20.

Peacock, W. F. (2004). "Heart failure management in the emergency department observation unit." Prog. Cardio. Dis. 46: 465-485.

Peelen, D. and L. M. Smith (2005). "Immobilization of Amine-Modified Oligonucleotides on Aldehyde-Terminated Alkanethiol Monolayers on Gold." Langmuir 21: 266-271.

Polanczyk, C. A., T. H. Lee, et al. (1998). "Cardiac Troponin I as a predictor of major cardiac events in emergency department patients with acute chest pain." J. Am. Coll. Cardiol. 32: 8-14.

Pope, J. H., T. P. Aufderheide, et al. (2000). "Missed diagnoses of actute cardiac ischemia in the emergency department." N. Engl. J. Med. 342: 1163-1170.

Remes, J., H. Miettinen, et al. (1991). "Validity of clinical diagnosis of heart failure in primary health care." Eur. Heart J. 12: 315-321.

Roberts, C., C. S. Chen, et al. (1998). "Using mixed self-assembled monolayers presenting RGD and (EG)(3)OH groups to characterize long-term attachment of bovine capillary endothelial cells to surfaces." Journal of the American Chemical Society 120(26): 6548-6555.

Rodriguez, E. B. and R. V. Stick (1990). "The Synthesis of Active-Site Directed Inhibitors of Some Beta-Glucan Hydrolases." Australian Journal of Chemistry 43(4): 665-679.

Sader, J. E. (1998). "Frequency response of cantilever beams immersed in viscous fluids with applications to the atomic force microscope." Journal of Applied Physics 84(1): 64-76.

Savonitto, S., D. Ardission, et al. (1999). "Prognostic value of the admission electrocardiogram in acute coronary syndromes." JAMA 281: 707-713.

Schmid, E. L., T. A. Keller, et al. (1997). "Reversible oriented surface immobilization of functional proteins on oxide surfaces." Analytical Chemistry 69(11): 1979-1985.

Schmitt, L., M. Ludwig, et al. (2000). "A metal-chelating microscopy tip as a new toolbox for single-molecule experiments by atomic force microscopy." Biophysical Journal 78(6): 3275-3285.

Seetharaman, J., Kaingsberg, A., et al. (1998). J Biol Chem 273:13047-13052.

Spitznagel, T. M., J. W. Jacobs, et al. (1993). "Random and site-specific immobilization of catalytic antibodies." Enzyme Microb. Technol. 15: 916-921.

Stevens, M. M., S. Allen, et al. (2000). "Probing protein-peptide-protein molecular architecture by atomic force microscopy and surface plasmon resonance." Analyst 125: 245-250.

Timmis, A. D. (1990). "Early diagnosis of acute myocardial infarction." Br. Med. J. 301: 941-942.

Turková, J. (1999). "Oriented immobilization of biologically active proteins as a tool for revealing protein interactions and function." J. Chromatograph. B. 722: 11-31.

Van Blerk, M., V. Maes, et al. (1992). "Analytical and clinical evaluation of creatine kinase MB mass assay by IMx: comparison with MB isoenzyme activity and serum myoglobin for early diagnosis of myocardial infarction." Clin. Chem. 38: 2380-2386.

Venge, P., B. Lindahl, et al. (2001). "New generation cardiac troponin I assay for the access immunoassay system." Clin. Chem. 47: 959-961.

Wagner, P., M. Hegner, et al. (1996). "Covalent immobilization of native biomolecules onto Au(111) via N-hydroxysuccinimide ester functionalized self-assembled monolayers for scanning probe microscopy." Biophys. J. 70: 2052-2066.

Williams, P. M. (2003). Anal Chim Acta 479:107-115.

Wimalasena, R. L. and G. S. Wilson (1991). "Factors affecting the specific activity of immobilized antibodies and their biologically active fragments." J. Chromatograph. 572: 85-102.

Wong, S. S., E. Joselevich, et al. (1998). "Covalently functionalized nanotubes as nanometre-sized probes in chemistry and biology." Nature 394(6688): 52-55.

Wong, S. S. J., Ernesto; Woolley, Adam T.; Cheung, Chhin Li; Lieber, Charles M. (1998). "Covalently functionalized nanotubes as nanometer-sized probes in chemistry and biology." Nature 394(6688): 52-55.

Wu, A. H. B. (1999). "Laboratory and near patient testing for cardiac markers." J. Clin. Lig. Assay 22: 3237.

Wu, A. H. B., F. S. Apple, et al. (1999). "National Academy of Clinical Biochemistry Standards of Laboratory Practice recommendations for use of cardiac markers in coronary artery disease." Clin. Chem. 45: 1104-1121.

Yu, Y. B., Privalov, P. L., Hodges, R. S. (2001). Biophys J 81:1632-1642.

Zhang, R., M. L. Brennan, et al. (2001). "Association between myeloperoxidase levels and risk of coronary artery disease." JAMA 286: 2136-2142.

Zhang, X., Bogorin, D. F., Moy, V. T. (2004). ChemPhys Chem 5; 175-182.

That which is claimed is:

1. A method for detecting a concentration of a member of a specific binding pair in a sample, the method comprising:

positioning a cantilever array adjacent a surface in the presence of a sample, wherein the cantilever array comprises a plurality of cantilevers having a first member of a specific binding pair thereon and the surface comprises a second member of the specific binding pair;

detecting a number of binding events between the first member of the specific binding pair on the plurality of cantilevers and the second member of the specific binding pair on the surface; and determining a concentration of the first and/or second member of the specific binding pair in the sample based on the detected number of binding events between the first member of the specific binding pair on the plurality of cantilevers and the second member of the specific binding pair on the surface wherein a binding event between the first member of the specific binding pair on one of the plurality of cantilevers and the second member of the specific binding pair on the surface causes deflection of a respective cantilever toward the surface, and detecting one of the binding events comprises:

applying a force to at least one of the cantilever array and/or the surface in a direction generally opposite the other of the cantilever array and/or the surface; and detecting a separation of one or more of the plurality of cantilevers from the surface.

2. The method of claim 1, wherein determining a concentration of the first and/or second member of the specific binding pair in the sample includes comparing the detected number of binding events to experimentally determined numbers of binding events for a known sample concentration of the first and/or second member of the specific binding pair.

3. The method of claim 1, wherein detecting a separation includes detecting an average separation force of the plurality of cantilevers.

4. The method of claim 1, wherein determining a concentration of the first and/or second member of the specific binding pair is based on the detected separation of one or more of the plurality of cantilevers from the surface.

5. The method of claim 1, wherein the plurality of cantilevers comprises a first plurality of cantilevers, the specific binding pair comprises a first specific binding pair, and the cantilever array includes a second plurality of cantilevers having a first member of a second specific binding pair thereon and the surface comprises a second member of the second specific binding pair, the method further comprising:

detecting a number of binding events between the first member of the second specific binding pair on the second plurality of cantilevers and the second member of the second specific binding pair on the surface; and determining a concentration of the first and/or second member of the second specific binding pair in the sample based on the detected number of binding events between the first member of the second specific binding pair on the second plurality of cantilevers and the second member of the second specific binding pair on the surface.

6. The method of claim 1, wherein the sample comprises a biological fluid.

7. The method of claim 6, wherein the biological fluid comprises blood.

8. The method of claim 1, wherein detecting one of the binding events includes detecting a deflection of the plurality of cantilevers using piezoelectric and/or piezomagnetic detection.

9. A system for detecting a member of a specific binding pair in a sample, the system comprising:
 a sample chamber configured to hold a sample therein;
 at least one cantilever having a first member of a specific binding pair thereon, wherein the surface comprises a second member of the specific binding pair;
 a controller configured to detect a number of binding events between the first member of the specific binding pair on the cantilever and the second member of the specific binding pair on the surface to determine a concentration of the first and/or second member of the specific binding pair in the sample based on the number of detected binding events between the first member of the specific binding pair on the cantilever and the second member of the specific binding pair on the surface wherein a binding event between the first member of the specific binding pair on the at least one cantilever and the second member of the specific binding pair on the surface causes deflection of a respective cantilever toward the surface, and the controller is configured to detect one of the binding events by:
 applying a force to at least one of the cantilever and/or the surface in a direction generally opposite the other of the cantilever and/or the surface; and
 detecting a separation of the at least one cantilever from the surface.

10. The system of claim 9, wherein the controller is configured to determine a concentration of the first and/or second member of the specific binding pair in the sample by comparing the number of detected binding events to experimentally determined numbers of detected binding events for a known sample concentration of the first and/or second member of the specific binding pair.

11. The system of claim 9, wherein the controller is configured to detect a separation by detecting an average separation force of the at least one cantilever for a plurality of binding.

12. The system of claim 9, wherein the controller is configured to determine a concentration of the first and/or second member of the specific binding pair based on the detected separation of the at least one cantilever from the surface for a plurality of binding.

13. The system of claim 9, wherein the at least one cantilever comprises a first plurality of cantilevers, the specific binding pair comprises a first specific binding pair, and a cantilever array includes the first plurality of cantilever and a second plurality of cantilevers having a first member of a second specific binding pair thereon and the surface comprises a second member of the second specific binding pair, wherein the controller is further configured to:
 detect a number of binding events between the first member of the second specific binding pair on the second plurality of cantilevers and the second member of the second specific binding pair on the surface; and to
 determine a concentration of the first and/or second member of the second specific binding pair in the sample based on the detected number of binding events between the first member of the second specific binding pair on the second plurality of cantilevers and the second member of the second specific binding pair on the surface.

14. The system of claim 9, wherein the sample comprises a biological fluid.

15. The system of claim 14, wherein the biological fluid comprises blood.

16. The system of claim 9, wherein detecting one of the binding events includes detecting a deflection of the at least one cantilever using piezoelectric and/or piezomagnetic detection.

17. The system of claim 9, wherein the at least one cantilever comprises a plurality of cantilevers and the controller is configured to detect a number and/or probability of binding between the first and second members of the specific binding pair for the plurality of cantilevers.

18. The system of claim 9, wherein the controller is configured to repeatedly position the at least one cantilever adjacent the surface in the presence of the sample to detect a number and/or probability of binding between the first and second members of the specific binding pair.

19. A method for detecting a concentration of a member of a specific binding pair in a sample, the method comprising:
 positioning a cantilever adjacent a surface in the presence of a sample, wherein the cantilever has a first member of a specific binding pair thereon and the surface comprises a second member of the specific binding pair;
 repeating the positioning step to detect a number of binding events between the first member of the specific binding pair on the cantilever and the second member of the specific binding pair on the surface; and
 determining a concentration of the first and/or second member of the specific binding pair in the sample based on the detected number of binding events between the first member of the specific binding pair on the cantilever and the second member of the specific binding pair on the surface wherein a binding event between the first member of the specific binding pair on one of the plurality of cantilevers and the second member of the specific binding pair on the surface causes deflection of a respective cantilever toward the surface, and detecting one of the binding events comprises:
 applying a force to at least one of the cantilever array and/or the surface in a direction generally opposite the other of the cantilever array and/or the surface; and
 detecting a separation of one or more of the plurality of cantilevers from the surface.

* * * * *